US009273300B2

(12) United States Patent
Maples et al.

(10) Patent No.: US 9,273,300 B2
(45) Date of Patent: Mar. 1, 2016

(54) METHODS AND COMPOSITIONS FOR MODULATING SIALIC ACID PRODUCTION AND TREATING HEREDITARY INCLUSION BODY MYOPATHY

(75) Inventors: Phillip Maples, Pilot Point, TX (US); Chris Jay, Grapevine, TX (US); John J. Nemunaitis, Cedar Hill, TX (US)

(73) Assignee: STRIKE BIO, INC, Dallas, TX (US)

( * ) Notice: Subject to any disclaimer, the term of this patent is extended or adjusted under 35 U.S.C. 154(b) by 977 days.

(21) Appl. No.: 12/526,239

(22) PCT Filed: Feb. 7, 2008

(86) PCT No.: PCT/US2008/001650
§ 371 (c)(1),
(2), (4) Date: Oct. 20, 2010

(87) PCT Pub. No.: WO2008/097623
PCT Pub. Date: Aug. 14, 2008

(65) Prior Publication Data
US 2011/0027373 A1 Feb. 3, 2011

Related U.S. Application Data

(60) Provisional application No. 60/900,034, filed on Feb. 7, 2007.

(51) Int. Cl.
*A61K 48/00* (2006.01)
*A61K 9/16* (2006.01)
*A61K 9/50* (2006.01)
*C12N 9/90* (2006.01)
*C12N 15/85* (2006.01)

(52) U.S. Cl.
CPC ............... *C12N 9/90* (2013.01); *A61K 48/005* (2013.01); *C12N 15/85* (2013.01)

(58) Field of Classification Search
CPC .................................................. A61K 48/005
USPC ...................................................... 514/44 R
See application file for complete search history.

(56) References Cited

U.S. PATENT DOCUMENTS

| | | | |
|---|---|---|---|
| 5,885,613 A | 3/1999 | Holland et al. | |
| 6,255,096 B1 * | 7/2001 | Hopwood et al. | 435/206 |
| 6,287,591 B1 | 9/2001 | Semple et al. | |
| 6,534,484 B1 | 3/2003 | Wheeler et al. | |
| 6,586,001 B1 | 7/2003 | Zalipsky | |
| 6,586,410 B1 | 7/2003 | Wheeler et al. | |
| 6,815,432 B2 | 11/2004 | Wheeler et al. | |
| 6,858,224 B2 | 2/2005 | Wheeler et al. | |
| 6,858,225 B2 | 2/2005 | Semple et al. | |
| 7,341,738 B2 | 3/2008 | Semple et al. | |
| 7,364,750 B2 | 4/2008 | Finn et al. | |
| 7,404,969 B2 | 7/2008 | Chen et al. | |
| 7,745,651 B2 | 6/2010 | Heyes et al. | |
| 7,803,397 B2 | 9/2010 | Heyes et al. | |
| 7,901,708 B2 | 3/2011 | MacLachlan et al. | |
| 2003/0077829 A1 | 4/2003 | MacLachlan | |
| 2003/0104044 A1 | 6/2003 | Semple et al. | |
| 2005/0008689 A1 | 1/2005 | Semple et al. | |
| 2005/0064595 A1 | 3/2005 | MacLachlan et al. | |
| 2005/0118253 A1 | 6/2005 | MacLachlan et al. | |
| 2006/0051405 A1 | 3/2006 | MacLachlan et al. | |
| 2006/0083780 A1 | 4/2006 | Heyes et al. | |

FOREIGN PATENT DOCUMENTS

WO 9807408 A1 2/1998
WO 9823765 A1 6/1998

OTHER PUBLICATIONS

Hong et al., 2003, The Journal of Biological Chemistry, 278:53045-53054.*
Invitrogen User Catalog for pcDNA 3.1(+) and pcDNA 3.1(-) [online], Version K, 2010 [retrieved on Sep. 19, 2011]. Retrieved from the Internet< URL: http://tools.invitrogen.com/content/sfs/manuals/pcdna3_1_man.pdf.>, pp. 1-23.*
Feero et al., 1997, Gene Therapy, 4: 664-674.*
Nemunaitis (2011, Human Gene Therapy, 22:1331-1341.*
Nemunaitis, J Gene Med, 2010, 12:403-412.*
Jay, Chris, et al., "Preclinical Assessment of wt GNE Gene Plasmid for Management of Hereditary Inclusion Body Myopathy 2 (HIBM2)," Gene Regulation and Systems Biology 2008, vol. 2, (2008), pp. 243-252.
Wheeler, JJ., et al., "Stabilized Plasmid-Lipid Particles: Construction and Characterization," Gene Therapy (1999), pp. 271-281.
Supplementary European Search Report for Application No. EP08725300, dated Jul. 27, 2011.
Coulombe, Zoe, et al., "564. Correction of Hyposialylation in Hereditary Inclusion Body Myopathy, by Ex-Vivo Therapy," Molecular Therapy, May 2006, vol. 33, Supplement 1, 3 pages.
Maples, Phillip B., et al., "560. GNE Gene Replacement in Hereditary Inclusion Body Myopathy," Molecular Therapy, May 2006, vol. 33, Supplement 1, 3 pages.
Edwan, J., et al., "Treatment with Flt3 Ligand Plasmid Reverses Allergic Airway Inflammation in Ovalbumin-Sensitized and Challenged Mice", International Immunopharmacology, 2005, 5:345-357.
Feero, WG., et al., "Selection and Use of Ligands for Receptor-Mediated Gene Delivery to Myogenic Cells", Gene Therapy, 1997, 4:664-674.

(Continued)

*Primary Examiner* — Valarie Bertoglio
(74) *Attorney, Agent, or Firm* — Edwin S. Flores; Chalker Flores LLP

(57) ABSTRACT

According to certain embodiments of the present invention, methods for modulating the production of sialic acid in a system are provided, which comprise providing the system with a wild-type GNE-encoding nucleic acid sequence. According to such embodiments, the system may comprise a cell, muscular tissue, or other desirable targets. Similarly, the present invention encompasses methods for producing wild-type GNE in a system that comprises a mutated endogenous GNE-encoding sequence. In other words, the present invention includes providing, for example, a cell or muscular tissue that harbors a mutated (defective) GNE-encoding sequence with a functional wild-type GNE encoding sequence.

14 Claims, 14 Drawing Sheets

(56) References Cited

OTHER PUBLICATIONS

Hong, Y., et al., "Lec3 Chinese Hamster Ovary Mutants Lack UDP-N.Acetylglucosamine 2-Epimerase Activity Because of Mutations in the Epimerase Domain of the Gne Gene", The Journal of Biological Chemistry, 20.3, 278 (52):53045-53054.

Invitrogen, Catalog Nos. V790-20 and V795-20, Version K, Nov. 10, 2010, 28-0104.

* cited by examiner

RE-PTL-100: Single Intramuscular injection with GNE GMP DNA in Plasma -Lyte A

| Mice Injected on | Dose given IM | OD400 On 11/12/07 | Number of Mice | Average pre-treatment weight in grams (range) | Toxicity at 24-48 hrs | Toxicity at WK 1 | Toxicity at WK 2 |
|---|---|---|---|---|---|---|---|
| N/A | Uninjected | | 6F | 17.4 (16.5- 19.2) | None | None | none |
| | | | 6M | 25.8 (23.8-27.9) | None | None | None |
| 11/13/07 and 11/14/07 | 0 ug GMP DNA PL | | 6F | 18.1 (16.1- 20) | None | None | None |
| | | | 6M | 25.4 (23.4-27.2) | None | None | None |
| 11/13/07 | 10 ug GMP DNA PL | | 6F | 18.5 (16.9-19.3) | None | None | None |
| | | | 6M | 26.1 (24.3- 27.9) | None | None | |
| 11/14/07 | 40 ug GMP DNA PL | 0.783 | 6F | 17.8 (16.6 -18.3) | None | None | None |
| | | | 6M | 26.2 (25.1-27.1) | None | None | None |

FIG. 7

RE-PTL-101: Single Intravenous Injection of GNE GMP DNA in PL

| Date Injections performed | Dose given IV | OD400 on 11/18/07 | Mice | Average pre-treatment weight (gms) | Toxicity at | | | |
|---|---|---|---|---|---|---|---|---|
| | | | | | 24 hrs | 48 hrs | WK 1 | WK 2 |
| 11/20/07 | 10 ug GMP DNA PL | | 6F | 17.7 (16.6 – 18.5g) | None | None | None | None |
| | | | 6M | 26.4 (25- 27.6) | None | None | None | None |
| 11/19/07 (F) and 11/20/07 (M) | 40 ug GMP DNA PL | | 6F | 18.2 (16.6 -19.9) | 2F showed acute toxicity** | None | None | None |
| | | | 6M | 26.1 (24.2-28.3) | None | None | None | None |
| 11/19/07 | 100 ug GMP DNA PL | 0.933 | 6F | 17.8 (17.1- 20.4) | 3F died, 2F showed acute toxicity ** | 1F died | None | None |
| | | | 6M | 25.5 (23.5-28.3) | All 6M showed acute toxicity** | None | None | None |
| 11/21/07 (F) and 11/29/07 (M) | 0 ug GMP DNA PL | | 6F | 17.9 (17.2-19.8) | None | None | None | None |
| | | | 6M | 26.7 (25.6-27.6) | None | None | None | None |

** Acute Toxicity: slow movement, ruffled coat, hunched back recovered by 48 hrs

FIG. 8

5e-4 GNE-wt (+ control)

5e-7 GNE-wt (- control)

26 F (0ug GNE)

2 F (10ug GNE)

5 F (10ug GNE)

15 F (40ug GNE)

17 F (40ug GNE)

Females

32 F (0ug GNE)

10 F (10ug GNE)

11 F (10ug GNE)

21 F (40ug GNE)

22 F (40ug GNE)

Males

Mouse #

FIG. 14

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial
<220> FEATURE:
<223> OTHER INFORMATION: PCR Primer

<400> SEQUENCE: 1
tgtgaggacc atgatcgcat cctt                                          24

<210> SEQ ID NO 2
<211> LENGTH: 24
```

```
<212> TYPE: DNA
<213> ORGANISM: Artificial
<220> FEATURE:
<223> OTHER INFORMATION: PCR Primer

<400> SEQUENCE: 2
acctccgagt tgcaatagtc agca                                              24

<210> SEQ ID NO 3
<211> LENGTH: 24
<212> TYPE: DNA
<213> ORGANISM: Artificial
<220> FEATURE:
<223> OTHER INFORMATION: PCR Primer

<400> SEQUENCE: 3
aatcaggccc atccagagac acaa                                              24

<210> SEQ ID NO 4
<211> LENGTH: 24
<212> TYPE: DNA
<213> ORGANISM: Artificial
<220> FEATURE:
<223> OTHER INFORMATION: PCR Primer

<400> SEQUENCE: 4
ttccaatctg acgtgttccc aggt                                              24

<210> SEQ ID NO 5
<211> LENGTH: 24
<212> TYPE: DNA
<213> ORGANISM: Artificial
<220> FEATURE:
<223> OTHER INFORMATION: PCR Primer

<400> SEQUENCE: 5
cgccaccaga cataatagct gaca                                              24

<210> SEQ ID NO 6
<211> LENGTH: 24
<212> TYPE: DNA
<213> ORGANISM: Artificial
<220> FEATURE:
<223> OTHER INFORMATION: PCR Primer

<400> SEQUENCE: 6
tagccagaag tcagatgctc aagg                                              24

<210> SEQ ID NO 7
<211> LENGTH: 22
<212> TYPE: DNA
<213> ORGANISM: Artificial
<220> FEATURE:
<223> OTHER INFORMATION: PCR Primer

<400> SEQUENCE: 7
cggaagaagg gcattgagca tc                                                22

<210> SEQ ID NO 8
<211> LENGTH: 22
<212> TYPE: DNA
<213> ORGANISM: Artificial
<220> FEATURE:
<223> OTHER INFORMATION: PCR Primer

<400> SEQUENCE: 8
```

```
tttgtcttgg gtgtcagcat cc                                         22
```

<210> SEQ ID NO 9
<211> LENGTH: 6217
<212> TYPE: DNA
<213> ORGANISM: Artificial
<220> FEATURE:
<223> OTHER INFORMATION: PUMVC3-wt-DNA construct (plasmid)

<400> SEQUENCE: 9

```
tggccattgc atacgttgta tccatatcat aatatgtaca tttatattgg ctcatgtcca    60
acattaccgc catgttgaca ttgattattg actagttatt aatagtaatc aattacgggg   120
tcattagttc atagcccata tatggagttc cgcgttacat aacttacggt aaatggcccg   180
cctggctgac cgcccaacga ccccCgccca ttgacgtcaa taatgacgta tgttcccata   240
gtaacgccaa tagggacttt ccattgacgt caatgggtgg agtatttacg gtaaactgcc   300
cacttggcag tacatcaagt gtatcatatg ccaagtacgc cccctattga cgtcaatgac   360
ggtaaatggc ccgcctggca ttatgcccag tacatgacct tatgggactt tcctacttgg   420
cagtacatct acgtattagt catcgctatt accatggtga tgcggttttg gcagtacatc   480
aatgggcgtg gatagcggtt tgactcacgg ggatttccaa gtctccaccc cattgacgtc   540
aatgggagtt tgttttggca ccaaaatcaa cgggactttc caaaatgtcg taacaactcc   600
gccccattga cgcaaatggg cggtaggcgt gtacggtggg aggtctatat aagcagagct   660
cgtttagtga accgtcagat cgcctggaga cgccatccac gctgttttga cctccataga   720
agacaccggg accgatccag cctccgcggc cgggaacggt gcattggaac gcggattccc   780
cgtgccaaga gtgacgtaag taccgcctat agactctata ggcacacccc tttggctctt   840
atgcatgcta tactgttttt ggcttggggc ctatacaccc ccgcttcctt atgctatagg   900
tgatggtata gcttagccta taggtgtggg ttattgacca ttattgacca ctccaacggt   960
ggagggcagt gtagtctgag cagtactcgt tgctgccgcg cgcgccacca gacataatag  1020
ctgacagact aacagactgt tcctttccat gggtcttttc tgcagtcacc gtcgtcgacg  1080
gtatcgataa gcttgatatc gaattcgccc ttatggagaa gaatgaaaat aaccgaaagc  1140
tgcgggtttg tgttgctact tgtaaccgtg cagattattc taaacttgcc ccgatcatgt  1200
ttggcattaa aaccgaacct gagttctttg aacttgatgt tgtggtactt ggctctcacc  1260
tgatagatga ctatggaaat acatatcgaa tgattgaaca agatgacttt gacattaaca  1320
ccaggctaca cacaattgtg aggggagaag atgaggcagc catggtggag tcagtaggcc  1380
tggccctagt gaagctgcca gatgtcctta atcgcctgaa gcctgatatc atgattgttc  1440
atggagacag gtttgatgcc ctggctctgg ccacatctgc tgccttgatg aacatccgaa  1500
tccttcacat tgaaggtggg gaagtcagtg ggaccattga tgactctatc agacatgcca  1560
taacaaaact ggctcattat catgtgtgct gcacccgcag tgcagagcag cacctgatat  1620
ccatgtgtga ggaccatgat cgcatccttt tggcaggctg cccttcctat gacaaacttc  1680
tctcagccaa gaacaaagac tacatgagca tcattcgcat gtggctaggt gatgatgtaa  1740
aatctaaaga ttcattgtt gcactacagc accctgtgac cactgacatt aagcattcca  1800
taaaaatgtt tgaattaaca ttggatgcac ttatctcatt taacaagcgg accctagtcc  1860
tgtttccaaa tattgacgca gggagcaaag atggttcg agtgatgcgg aagaagggca  1920
ttgagcatca tcccaacttt cgtgcagtta aacacgtccc atttgaccag tttatacagt  1980
tggttgccca tgctggctgt atgattggga acagcagctg tggggttcga aagttggag  2040
```

```
cttttggaac acctgtgatc aacctgggaa cacgtcagat tggaagagaa acagggggaga    2100
atgttcttca tgtccgggat gctgacaccc aagacaaaat attgcaagca ctgcaccttc    2160
agtttggtaa acagtaccct tgttcaaaga tatatgggga tggaaatgct gttccaagga    2220
ttttgaagtt tctcaaatct atcgatcttc aagagccact gcaaagaaa ttctgctttc     2280
ctcctgtgaa ggagaatatc tctcaagata ttgaccatat tcttgaaact ctaagtgcct    2340
tggccgttga tcttggcggg acgaacctcc gagttgcaat agtcagcatg aagggtgaaa    2400
tagttaagaa gtatactcag ttcaatccta aaacctatga agagaggatt aatttaatcc    2460
tacagatgtg tgtggaagct gcagcagaag ctgtaaaact gaactgcaga attttgggag    2520
taggcatttc cacaggtggc cgtgtaaatc ctcgggaagg aattgtgctg cattcaacca    2580
aactgatcca agagtggaac tctgtggacc ttaggacccc cctttctgac actttgcatc    2640
tccctgtgtg ggtagacaat gatggcaact gtgctgccct ggcggaaagg aaatttggcc    2700
aaggaaaggg actggaaaac tttgttacac ttatcacagg cacaggaatc ggtggtggaa    2760
ttatccatca gcatgaattg atccacggaa gctccttctg tgctgcagaa ctgggccacc    2820
ttgttgtgtc tctggatggg cctgattgtt cctgtggaag ccatgggtgc attgaagcat    2880
acgcctctgg aatggccttg cagagggagg caaaaaagct ccatgatgag gacctgctct    2940
tggtggaagg gatgtcagtg ccaaaagatg aggctgtggg tgcgctccat ctcatccaag    3000
ctgcgaaaact tggcaatgcg aaggcccaga gcatcctaag aacagctgga acagctttgg    3060
gtcttggggt tgtgaacatc ctccatacca tgaatccctc ccttgtgatc ctctccggag    3120
tcctggccag tcactatatc cacattgtca aagacgtcat tcgccagcag gccttgtcct    3180
ccgtgcagga cgtggatgtg gtggtttcgg atttggttga ccccgccctg ctgggtgctg    3240
ccagcatggt tctggactac acaacacgca ggatctacta gaagggcgaa ttcacgtggg    3300
cccggtaccg tatactctag agcggccgcg gatccagatc ttttccctc tgccaaaaat     3360
tatggggaca tcatgaagcc ccttgagcat ctgacttctg gctaataaag gaaatttatt    3420
ttcattgcaa tagtgtgttg gaatttttg tgtctctcac tcggaaggac atatgggagg     3480
gcaaatcatt taaaacatca gaatgagtat ttggtttaga gtttggcaac atatgcccat    3540
tcttccgctt cctcgctcac tgactcgctg cgctcggtcg ttcggctgcg gcgagcggta    3600
tcagctcact caaaggcggt aatacggtta tccacagaat caggggataa cgcaggaaag    3660
aacatgtgag caaaaggcca gcaaaaggcc aggaaccgta aaaaggccgc gttgctggcg    3720
tttttccata ggctccgccc ccctgacgag catcacaaaa atcgacgctc aagtcagagg    3780
tggcgaaacc cgacaggact ataaagatac caggcgtttc ccctggaag ctccctcgtg     3840
cgctctcctg ttccgaccct gccgcttacc ggatacctgt ccgcctttct cccttcggga    3900
agcgtggcgc tttctcatag ctcacgctgt aggtatctca gttcggtgta ggtcgttcgc    3960
tccaagctgg gctgtgtgca cgaacccccc gttcagcccg accgctgcgc cttatccggt    4020
aactatcgtc ttgagtccaa cccggtaaga cacgacttat cgccactggc agcagccact    4080
ggtaacagga ttagcagagc gaggtatgta ggcggtgcta cagagttctt gaagtggtgg    4140
cctaactacg gctacactag aagaacagta tttggtatct gcgctctgct gaagccagtt    4200
accttcggaa aaagagttgg tagctcttga tccggcaaac aaaccaccgc tggtagcggt    4260
ggttttttg tttgcaagca gcagattacg cgcagaaaaa aaggatctca agaagatcct    4320
ttgatctttt ctacggggtc tgacgctcag tggaacgaaa actcacgtta agggattttg    4380
```

```
gtcatgagat tatcaaaaag gatcttcacc tagatccttt taaattaaaa atgaagtttt    4440
aaatcaatct aaagtatata tgagtaaact tggtctgaca gttaccaatg cttaatcagt    4500
gaggcaccta tctcagcgat ctgtctattt cgttcatcca tagttgcctg actcgggggg    4560 gggggcgct gaggtctgcc tcgtgaagaa ggtgttgctg actcatacca ggcctgaatc     4620
gccccatcat ccagccagaa agtgagggag ccacggttga tgagagcttt gttgtaggtg    4680
gaccagttgg tgattttgaa cttttgcttt gccacggaac ggtctgcgtt gtcgggaaga    4740
tgcgtgatct gatccttcaa ctcagcaaaa gttcgattta ttcaacaaag ccgccgtccc    4800
gtcaagtcag cgtaatgctc tgccagtgtt acaaccaatt aaccaattct gattagaaaa    4860
actcatcgag catcaaatga aactgcaatt tattcatatc aggattatca ataccatatt    4920
tttgaaaaag ccgtttctgt aatgaaggag aaaactcacc gaggcagttc cataggatgg    4980
caagatcctg gtatcggtct gcgattccga ctcgtccaac atcaatacaa cctattaatt    5040 tccctcgtc aaaataagg ttatcaagtg agaaatcacc atgagtgacg actgaatccg      5100
gtgagaatgg caaaagctta tgcatttctt tccagacttg ttcaacaggc cagccattac    5160
gctcgtcatc aaaatcactc gcatcaacca aaccgttatt cattcgtgat tgcgcctgag    5220
cgagacgaaa tacgcgatcg ctgttaaaag gacaattaca acaggaatc gaatgcaacc     5280 ggcgcaggaa cactgccagc gcatcaacaa tattttcacc tgaatcagga tattcttcta    5340
atacctggaa tgctgttttc ccggggatcg cagtggtgag taaccatgca tcatcaggag    5400
tacggataaa atgcttgatg gtcggaagag gcataaattc cgtcagccag tttagtctga    5460
ccatctcatc tgtaacatca ttggcaacgc tacctttgcc atgtttcaga aacaactctg    5520
gcgcatcggg cttcccatac aatcgataga ttgtcgcacc tgattgcccg acattatcgc    5580
gagcccattt atacccatat aaatcagcat ccatgttgga atttaatcgc ggcctcgagc    5640
aagacgtttc ccgttgaata tggctcataa cacccccttgt attactgttt atgtaagcag    5700
acagttttat tgttcatgat gatatatttt tatcttgtgc aatgtaacat cagagatttt    5760
gagacacaac gtggctttcc cccccccccc attattgaag catttatcag ggttattgtc    5820
tcatgagcgg atacatattt gaatgtattt agaaaaataa acaaataggg gttccgcgca    5880
catttccccg aaaagtgcca cctgacgtct aagaaaccat tattatcatg acattaacct    5940
ataaaaatag gcgtatcacg aggccctttc gtctcgcgcg tttcggtgat gacggtgaaa    6000
acctctgaca catgcagctc ccggagacgg tcacagcttg tctgtaagcg gatgccggga    6060
gcagacaagc ccgtcagggc gcgtcagcgg tgttggcgg gtgtcggggc tggcttaact     6120
atgcggcatc agagcagatt gtactgagag tgcaccatat gcggtgtgaa ataccgcaca    6180
gatgcgtaag gagaaaatac cgcatcagat tggctat                             6217
```

<210> SEQ ID NO 10
<211> LENGTH: 2169
<212> TYPE: DNA
<213> ORGANISM: Homo sapiens

<400> SEQUENCE: 10

```
atggagaaga atggaaataa ccgaaagctg cgggtttgtg ttgctacttg taaccgtgca      60
gattattcta aacttgcccc gatcatgttt ggcattaaaa ccgaacctga gttctttgaa     120
cttgatgttg tggtacttgg ctctcacctg atagatgact atggaaatac atatcgaatg     180
attgaacaag atgactttga cattaacacc aggctacaca caattgtgag gggagaagat     240
gaggcagcca tggtggagtc agtaggcctg gccctagtga agctgccaga tgtccttaat     300
```

```
cgcctgaagc ctgatatcat gattgttcat ggagacaggt ttgatgccct ggctctggcc      360
acatctgctg ccttgatgaa catccgaatc cttcacattg aaggtgggga agtcagtggg      420
accattgatg actctatcag acatgccata acaaaactgg ctcattatca tgtgtgctgc      480
acccgcagtg cagagcagca cctgatatcc atgtgtgagg accatgatcg catccttttg      540
gcaggctgcc cttcctatga caaacttctc tcagccaaga caaagactac atgagcatc       600 attcgcatgt ggctaggtga tgatgtaaaa tctaaagatt acattgttgc actacagcac      660
cctgtgacca ctgacattaa gcattccata aaaatgtttg aattaacatt ggatgcactt      720
atctcattta caagcggac cctagtcctg tttccaaata ttgacgcagg gagcaaagag        780
atggttcgag tgatgcggaa aagggcatt gagcatcatc ccaactttcg tgcagttaaa        840
cacgtcccat ttgaccagtt tatacagttg gttgcccatg ctggctgtat gattgggaac      900
agcagctgtg gggttcgaga agttggagct tttggaacac ctgtgatcaa cctgggaaca      960
cgtcagattg aagagaaac aggggagaat gttcttcatg tccgggatgc tgacacccaa       1020
gacaaaatat tgcaagcact gcaccttcag tttggtaaac agtacccttg ttcaaagata      1080
tatggggatg aaatgctgt tccaaggatt ttgaagtttc tcaaatctat cgatcttcaa       1140
gagccactgc aaaagaaatt ctgctttcct cctgtgaagg agaatatctc tcaagatatt      1200
gaccatattc ttgaaactct aagtgccttg gccgttgatc ttggcgggac gaacctccga      1260
gttgcaatag tcagcatgaa gggtgaaata gttaagaagt atactcagtt caatcctaaa      1320
acctatgaag agaggattaa tttaatccta cagatgtgtg tggaagctgc agcagaagct      1380
gtaaaactga actgcagaat tttgggagta ggcatttcca caggtggccg tgtaaatcct      1440
cgggaaggaa ttgtgctgca ttcaaccaaa ctgatccaag agtggaactc tgtgaccttt      1500
aggacccccc tttctgacac tttgcatctc cctgtgtggg tagacaatga tggcaactgt      1560
gctgccctgg cggaaaggaa atttggccaa ggaaagggac tggaaaactt tgttacactt      1620
atcacaggca caggaatcgg tggtggaatt atccatcagc atgaattgat ccacggaagc      1680
tccttctgtg ctgcagaact gggccacctt gttgtgtctc tggatgggcc tgattgttcc      1740
tgtggaagcc atgggtgcat tgaagcatac gcctctggaa tggccttgca gagggaggca      1800
aaaaagctcc atgatgagga cctgctcttg gtgaaggga tgtcagtgcc aaaagatgag       1860
gctgtgggtg cgctccatct catccaagct gcgaaacttg gcaatgcgaa ggcccagagc      1920
atcctaagaa cagctggaac agctttgggt cttggggttg tgaacatcct ccataccatg      1980
aatccctccc ttgtgatcct ctccggagtc ctggccagtc actatatcca cattgtcaaa      2040
gacgtcattc gccagcaggc cttgtcctcc gtgcaggacg tggatgtggt ggtttcggat      2100
ttggttgacc ccgccctgct gggtgctgcc agcatggttc tggactacac aacacgcagg      2160
atctactag                                                              2169
```

<210> SEQ ID NO 11
<211> LENGTH: 722
<212> TYPE: PRT
<213> ORGANISM: Homo sapiens

<400> SEQUENCE: 11

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
                20                  25                  30

-continued

```
Lys Thr Glu Pro Glu Phe Phe Glu Leu Asp Val Val Leu Gly Ser
         35                  40                  45
His Leu Ile Asp Asp Tyr Gly Asn Thr Tyr Arg Met Ile Glu Gln Asp
 50                  55                  60
Asp Phe Asp Ile Asn Thr Arg Leu His Thr Ile Val Arg Gly Glu Asp
 65                  70                  75                  80
Glu Ala Ala Met Val Glu Ser Val Gly Leu Ala Leu Val Lys Leu Pro
                 85                  90                  95
Asp Val Leu Asn Arg Leu Lys Pro Asp Ile Met Ile Val His Gly Asp
                100                 105                 110
Arg Phe Asp Ala Leu Ala Leu Ala Thr Ser Ala Leu Met Asn Ile
             115                 120                 125
Arg Ile Leu His Ile Glu Gly Gly Glu Val Ser Gly Thr Ile Asp Asp
             130                 135                 140
Ser Ile Arg His Ala Ile Thr Lys Leu Ala His Tyr His Val Cys Cys
145                 150                 155                 160
Thr Arg Ser Ala Glu Gln His Leu Ile Ser Met Cys Glu Asp His Asp
                165                 170                 175
Arg Ile Leu Leu Ala Gly Cys Pro Ser Tyr Asp Lys Leu Leu Ser Ala
             180                 185                 190
Lys Asn Lys Asp Tyr Met Ser Ile Ile Arg Met Trp Leu Gly Asp Asp
         195                 200                 205
Val Lys Ser Lys Asp Tyr Ile Val Ala Leu Gln His Pro Val Thr Thr
     210                 215                 220
Asp Ile Lys His Ser Ile Lys Met Phe Glu Leu Thr Leu Asp Ala Leu
225                 230                 235                 240
Ile Ser Phe Asn Lys Arg Thr Leu Val Leu Phe Pro Asn Ile Asp Ala
                245                 250                 255
Gly Ser Lys Glu Met Val Arg Val Met Arg Lys Lys Gly Ile Glu His
             260                 265                 270
His Pro Asn Phe Arg Ala Val Lys His Val Pro Phe Asp Gln Phe Ile
         275                 280                 285
Gln Leu Val Ala His Ala Gly Cys Met Ile Gly Asn Ser Ser Cys Gly
     290                 295                 300
Val Arg Glu Val Gly Ala Phe Gly Thr Pro Val Ile Asn Leu Gly Thr
305                 310                 315                 320
Arg Gln Ile Gly Arg Glu Thr Gly Glu Asn Val Leu His Val Arg Asp
                325                 330                 335
Ala Asp Thr Gln Asp Lys Ile Leu Gln Ala Leu His Leu Gln Phe Gly
             340                 345                 350
Lys Gln Tyr Pro Cys Ser Lys Ile Tyr Gly Asp Gly Asn Ala Val Pro
         355                 360                 365
Arg Ile Leu Lys Phe Leu Lys Ser Ile Asp Leu Gln Glu Pro Leu Gln
     370                 375                 380
Lys Lys Phe Cys Phe Pro Pro Lys Glu Asn Ile Ser Gln Asp Ile
385                 390                 395                 400
Asp His Ile Leu Glu Thr Leu Ser Ala Leu Ala Val Asp Leu Gly Gly
                405                 410                 415
Thr Asn Leu Arg Val Ala Ile Val Ser Met Lys Gly Glu Ile Val Lys
             420                 425                 430
Lys Tyr Thr Gln Phe Asn Pro Lys Thr Tyr Glu Glu Arg Ile Asn Leu
         435                 440                 445
Ile Leu Gln Met Cys Val Glu Ala Ala Ala Glu Ala Val Lys Leu Asn
```

```
            450                 455                 460
Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
        515                 520                 525

Gly Gln Gly Lys Gly Leu Glu Asn Phe Val Thr Leu Ile Thr Gly Thr
    530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
    610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
        675                 680                 685

Ser Ser Val Gln Asp Val Asp Val Val Ser Asp Leu Val Asp Pro
    690                 695                 700

Ala Leu Leu Gly Ala Ala Ser Met Val Leu Asp Tyr Thr Thr Arg Arg
705                 710                 715                 720

Ile Tyr

<210> SEQ ID NO 12
<211> LENGTH: 2169
<212> TYPE: DNA
<213> ORGANISM: Homo sapiens

<400> SEQUENCE: 12
atggagaaga atggaaataa ccgaaagctg cgggtttgtg ttgctacttg taaccgtgca      60
gattattcta aacttgcccc gatcatgttt ggcattaaaa ccgaacctga gttctttgaa     120
cttgatgttg tggtacttgg ctctcacctg atagatgact atggaaatac atatcgaatg     180
attgaacaag atgactttga cattaacacc aggctacaca caattgtgag gggagaagat     240
gaggcagcca tggtggagtc agtaggcctg gccctagtga agctgccaga tgtccttaat     300
cgcctgaagc ctgatatcat gattgttcat ggagacaggt tgatgccct ggctctggcc      360 acatctgctg ccttgatgaa catccgaatc cttcacattg aaggtgggga agtcagtggg     420
accattgatg actctatcag acatgccata acaaaactgg ctcattatca tgtgtgctgc     480
acccgcagtg cagagcagca cctgatatcc atgtgtgagg accatgatcg catccttttg     540
gcaggctgcc cttcctatga caaacttctc tcagccaaga acaaagacta catgagcatc     600
```

```
attcgcatgt ggctaggtga tgatgtaaaa tctaaagatt acattgttgc actacagcac      660
cctgtgacca ctgacattaa gcattccata aaaatgtttg aattaacatt ggatgcactt      720
atctcattta acaagcggac cctagtcctg tttccaaata ttgacgcagg gagcaaagag      780
atggttcgag tgatgcagaa gaagggcatt gagcatcatc ccaactttcg tgcagttaaa      840
cacgtcccat ttgaccagtt tatacagttg gttgcccatg ctggctgtat gattgggaac      900
agcagctgtg gggttcgaga agttggagct tttggaacac tgtgatcaa cctgggaaca      960
cgtcagattg aagagaaac aggggagaat gttcttcatg tccgggatgc tgacacccaa     1020
gacaaaatat tgcaagcact gcaccttcag tttggtaaac agtacccttg ttcaaagata     1080
tatggggatg gaaatgctgt tccaaggatt ttgaagtttc tcaaatctat cgatcttcaa     1140
gagccactgc aaaagaaatt ctgctttcct cctgtgaagg agaatatctc tcaagatatt     1200
gaccatattc ttgaaactct aagtgccttg gccgttgatc ttggcgggac gaacctccga     1260
gttgcaatag tcagcatgaa gggtgaaata gttaagaagt atactcagtt caatcctaaa     1320
acctatgaag agaggattaa tttaatccta cagatgtgtg tggaagctgc agcagaagct     1380
gtaaaactga actgcagaat tttgggagta ggcatttcca caggtggccg tgtaaatcct     1440
cgggaaggaa ttgtgctgca ttcaaccaaa ctgatccaag agtggaactc tgtggacctt     1500
aggaccccc tttctgacac tttgcatctc cctgtgtggg tagacaatga tggcaactgt     1560
gctgccctgg cggaaaggaa atttggccaa ggaaagggac tggaaaactt tgttacactt     1620
atcacaggca caggaatcgg tggtggaatt atccatcagc atgaattgat ccacggaagc     1680
tccttctgtg ctgcagaact gggccacctt gttgtgtctc tggatgggcc tgattgttcc     1740
tgtgaagcc atgggtgcat tgaagcatac gcctctggaa tggccttgca gagggaggca     1800
aaaaagctcc atgatgagga cctgctcttg gtggaaggga tgtcagtgcc aaaagatgag     1860
gctgtgggtg cgctccatct catccaagct gcgaaacttg gcaatgcgaa ggcccagagc     1920
atcctaagaa cagctggaac agctttgggt cttggggttg tgaacatcct ccataccatg     1980
aatccctccc ttgtgatcct ctccggagtc ctggccagtc actatatcca cattgtcaaa     2040
gacgtcattc gccagcaggc cttgtcctcc gtgcaggacg tggatgtggt ggtttcggat     2100
ttggttgacc ccgccctgct gggtgctgcc agcatggttc tggactacac aacacgcagg     2160
atctactag                                                             2169
```

<210> SEQ ID NO 13
<211> LENGTH: 663
<212> TYPE: PRT
<213> ORGANISM: Homo sapiens

<400> SEQUENCE: 13

Met Ile Glu Gln Asp Asp Phe Asp Ile Asn Thr Arg Leu His Thr Ile
1               5                   10                  15

Val Arg Gly Glu Asp Glu Ala Ala Met Val Glu Ser Val Gly Leu Ala
            20                  25                  30

Leu Val Lys Leu Pro Asp Val Leu Asn Arg Leu Lys Pro Asp Ile Met
        35                  40                  45

Ile Val His Gly Asp Arg Phe Asp Ala Leu Ala Leu Ala Thr Ser Ala
    50                  55                  60

Ala Leu Met Asn Ile Arg Ile Leu His Ile Glu Gly Gly Glu Val Ser
65                  70                  75                  80

Gly Thr Ile Asp Asp Ser Ile Arg His Ala Ile Thr Lys Leu Ala His

```
                    85                  90                  95
Tyr His Val Cys Cys Thr Arg Ser Ala Glu Gln His Leu Ile Ser Met
                100                 105                 110
Cys Glu Asp His Asp Arg Ile Leu Leu Ala Gly Cys Pro Ser Tyr Asp
                115                 120                 125
Lys Leu Leu Ser Ala Lys Asn Lys Asp Tyr Met Ser Ile Ile Arg Met
            130                 135                 140
Trp Leu Gly Asp Asp Val Lys Ser Lys Asp Tyr Ile Val Ala Leu Gln
145                 150                 155                 160
His Pro Val Thr Thr Asp Ile Lys His Ser Ile Lys Met Phe Glu Leu
                165                 170                 175
Thr Leu Asp Ala Leu Ile Ser Phe Asn Lys Arg Thr Leu Val Leu Phe
                180                 185                 190
Pro Asn Ile Asp Ala Gly Ser Lys Glu Met Val Arg Val Met Gln Lys
            195                 200                 205
Lys Gly Ile Glu His His Pro Asn Phe Arg Ala Val Lys His Val Pro
        210                 215                 220
Phe Asp Gln Phe Ile Gln Leu Val Ala His Ala Gly Cys Met Ile Gly
225                 230                 235                 240
Asn Ser Ser Cys Gly Val Arg Glu Val Gly Ala Phe Gly Thr Pro Val
                245                 250                 255
Ile Asn Leu Gly Thr Arg Gln Ile Gly Arg Glu Thr Gly Glu Asn Val
            260                 265                 270
Leu His Val Arg Asp Ala Asp Thr Gln Asp Lys Ile Leu Gln Ala Leu
        275                 280                 285
His Leu Gln Phe Gly Lys Gln Tyr Pro Cys Ser Lys Ile Tyr Gly Asp
    290                 295                 300
Gly Asn Ala Val Pro Arg Ile Leu Lys Phe Leu Lys Ser Ile Asp Leu
305                 310                 315                 320
Gln Glu Pro Leu Gln Lys Lys Phe Cys Phe Pro Pro Val Lys Glu Asn
                325                 330                 335
Ile Ser Gln Asp Ile Asp His Ile Leu Glu Thr Leu Ser Ala Leu Ala
                340                 345                 350
Val Asp Leu Gly Gly Thr Asn Leu Arg Val Ala Ile Val Ser Met Lys
            355                 360                 365
Gly Glu Ile Val Lys Lys Tyr Thr Gln Phe Asn Pro Lys Thr Tyr Glu
        370                 375                 380
Glu Arg Ile Asn Leu Ile Leu Gln Met Cys Val Glu Ala Ala Ala Glu
385                 390                 395                 400
Ala Val Lys Leu Asn Cys Arg Ile Leu Gly Val Gly Ile Ser Thr Gly
                405                 410                 415
Gly Arg Val Asn Pro Arg Glu Gly Ile Val Leu His Ser Thr Lys Leu
            420                 425                 430
Ile Gln Glu Trp Asn Ser Val Asp Leu Arg Thr Pro Leu Ser Asp Thr
        435                 440                 445
Leu His Leu Pro Val Trp Val Asp Asn Asp Gly Asn Cys Ala Ala Leu
    450                 455                 460
Ala Glu Arg Lys Phe Gly Gln Gly Lys Gly Leu Glu Asn Phe Val Thr
465                 470                 475                 480
Leu Ile Thr Gly Thr Gly Ile Gly Gly Gly Ile Ile His Gln His Glu
                485                 490                 495
Leu Ile His Gly Ser Ser Phe Cys Ala Ala Glu Leu Gly His Leu Val
            500                 505                 510
```

```
Val Ser Leu Asp Gly Pro Asp Cys Ser Cys Gly Ser His Gly Cys Ile
        515                 520                 525

Glu Ala Tyr Ala Ser Gly Met Ala Leu Gln Arg Glu Ala Lys Lys Leu
    530                 535                 540

His Asp Glu Asp Leu Leu Leu Val Glu Gly Met Ser Val Pro Lys Asp
545                 550                 555                 560

Glu Ala Val Gly Ala Leu His Leu Ile Gln Ala Ala Lys Leu Gly Asn
                565                 570                 575

Ala Lys Ala Gln Ser Ile Leu Arg Thr Ala Gly Thr Ala Leu Gly Leu
            580                 585                 590

Gly Val Val Asn Ile Leu His Thr Met Asn Pro Ser Leu Val Ile Leu
        595                 600                 605

Ser Gly Val Leu Ala Ser His Tyr Ile His Ile Val Lys Asp Val Ile
    610                 615                 620

Arg Gln Gln Ala Leu Ser Ser Val Gln Asp Val Asp Val Val Ser
625                 630                 635                 640

Asp Leu Val Asp Pro Ala Leu Leu Gly Ala Ala Ser Met Val Leu Asp
                645                 650                 655

Tyr Thr Thr Arg Arg Ile Tyr
            660

<210> SEQ ID NO 14
<211> LENGTH: 2169
<212> TYPE: DNA
<213> ORGANISM: Homo sapiens

<400> SEQUENCE: 14
atggagaaga atggaaataa ccgaaagctg cgggtttgtg ttgctacttg taaccgtgca      60
gattattcta aacttgcccc gatcatgttt ggcattaaaa ccgaacctga gttctttgaa     120
cttgatgttg tggtacttgg ctctcacctg atagatgact atggaaatac atatcgaatg     180
attgaacaag atgactttga cattaacacc aggctacaca caattgtgag gggagaagat     240
gaggcagcca tggtggagtc agtaggcctg gccctagtga agctgccaga tgtccttaat     300
cgcctgaagc ctgatatcat gattgttcat ggagacaggt ttgatgccct ggctctggcc     360
acatctgctg ccttgatgaa catccgaatc cttcacattg aaggtgggga agtcagtggg     420
accattgatg actctatcag acatgccata acaaaactgg ctcattatca tgtgtgctgc     480
acccgcagtg cagagcagca cctgatatcc atgtgtgagg accatgatcg catccttttg     540
gcaggctgcc cttcctatga caaacttctc tcagccaaga caaagactg catgagcatc     600 attcgcatgt ggctaggtga tgatgtaaaa tctaaagatt acattgttgc actacagcac     660
cctgtgacca ctgacattaa gcattccata aaaatgtttg aattaacatt ggatgcactt     720
atctcattta caagcggac cctagtcctg tttccaaata ttgacgcagg gagcaaagag     780
atggttcgag tgatgcggaa gaagggcatt gagcatcatc ccaactttcg tgcagttaaa     840
cacgtcccat ttgaccagtt tatacagttg gttgcccatg ctggctgtat gattgggaac     900
agcagctgtg gggttcgaga agttggagct tttggaacac ctgtgatcaa cctgggaaca     960
cgtcagattg aagagaaac aggggagaat gttcttcatg tccgggatgc tgacacccaa    1020
gacaaaatat tgcaagcact gcaccttcag tttggtaaac agtacccttg ttcaaagata    1080 tatgggatg aaatgctgt tccaaggatt ttgaagttc tcaaatctat cgatcttcaa    1140
gagccactgc aaaagaaatt ctgctttcct cctgtgaagg agaatatctc tcaagatatt    1200
```

-continued

```
gaccatattc ttgaaactct aagtgccttg gccgttgatc ttggcgggac gaacctccga   1260
gttgcaatag tcagcatgaa gggtgaaata gttaagaagt atactcagtt caatcctaaa   1320
acctatgaag agaggattaa tttaatccta cagatgtgtg tggaagctgc agcagaagct   1380
gtaaaactga actgcagaat tttgggagta ggcatttcca caggtggccg tgtaaatcct   1440
cgggaaggaa ttgtgctgca ttcaaccaaa ctgatccaag agtggaactc tgtggacctt   1500 aggaccccc tttctgacac tttgcatctc cctgtgtggg tagacaatga tggcaactgt   1560
gctgccctgg cggaaaggaa atttggccaa ggaaagggac tggaaaactt tgttacactt   1620
atcacaggca caggaatcgg tggtggaatt atccatcagc atgaattgat ccacggaagc   1680
tccttctgtg ctgcagaact gggccacctt gttgtgtctc tggatgggcc tgattgttcc   1740
tgtggaagcc atgggtgcat tgaagcatac gcctctggaa tggccttgca gagggaggca   1800
aaaaagctcc atgatgagga cctgctcttg gtggaaggga tgtcagtgcc aaaagatgag   1860
gctgtgggtg cgctccatct catccaagct gcgaaacttg gcaatgcgaa ggcccagagc   1920
atcctaagaa cagctggaac agctttgggt cttgggttg tgaacatcct ccataccatg   1980
aatccctccc ttgtgatcct ctccggagtc ctggccagtc actatatcca cattgtcaaa   2040
gacgtcattc gccagcaggc cttgtcctcc gtgcaggacg tggatgtggt ggtttcggat   2100
ttggttgacc ccgccctgct gggtgctgcc agcacggttc tggactacac aacacgcagg   2160
atctactag                                                           2169
```

<210> SEQ ID NO 15
<211> LENGTH: 722
<212> TYPE: PRT
<213> ORGANISM: Homo sapiens

<400> SEQUENCE: 15

```
Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Ile Leu His Ile Glu Gly Gly Glu Val Ser Gly Thr Ile Asp Asp
    130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
```

```
                195                 200                 205
Val Lys Ser Lys Asp Tyr Ile Val Ala Leu Gln His Pro Val Thr Thr
210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Lys Gly Ile Glu His
                260                 265                 270

His Pro Asn Phe Arg Ala Val Lys His Val Pro Phe Asp Gln Phe Ile
            275                 280                 285

Gln Leu Val Ala His Ala Gly Cys Met Ile Gly Asn Ser Ser Cys Gly
        290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
        435                 440                 445

Ile Leu Gln Met Cys Val Glu Ala Ala Glu Ala Val Lys Leu Asn
450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
        515                 520                 525

Gly Gln Gly Lys Gly Leu Glu Asn Phe Val Thr Leu Ile Thr Gly Thr
530                 535                 540

Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
            580                 585                 590

Gly Met Ala Leu Gln Arg Glu Ala Lys Lys Leu His Asp Glu Asp Leu
        595                 600                 605

Leu Leu Val Glu Gly Met Ser Val Pro Lys Asp Glu Ala Val Gly Ala
610                 615                 620
```

```
Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
            645                 650                 655

Leu His Thr Met Asn Pro Ser Leu Val Ile Leu Ser Gly Val Leu Ala
            660                 665                 670

Ser His Tyr Ile His Ile Val Lys Asp Val Ile Arg Gln Gln Ala Leu
            675                 680                 685

Ser Ser Val Gln Asp Val Asp Val Val Ser Asp Leu Val Asp Pro
690                 695                 700

Ala Leu Leu Gly Ala Ala Ser Thr Val Leu Asp Tyr Thr Thr Arg Arg
705                 710                 715                 720

Ile Tyr

<210> SEQ ID NO 16
<211> LENGTH: 716
<212> TYPE: PRT
<213> ORGANISM: Homo sapiens

<400> SEQUENCE: 16

Asn Arg Lys Leu Arg Val Cys Val Ala Thr Cys Asn Arg Ala Asp Tyr
1               5                   10                  15

Ser Lys Leu Ala Pro Ile Met Phe Gly Ile Lys Thr Glu Pro Glu Phe
            20                  25                  30

Phe Glu Leu Asp Val Val Leu Gly Ser His Leu Ile Asp Asp Tyr
        35                  40                  45

Gly Asn Thr Tyr Arg Met Ile Glu Gln Asp Asp Phe Asp Ile Asn Thr
50                  55                  60

Arg Leu His Thr Ile Val Arg Gly Glu Asp Ala Ala Met Val Glu
65                  70                  75                  80

Ser Val Gly Leu Ala Leu Val Lys Leu Pro Asp Val Leu Asn Arg Leu
            85                  90                  95

Lys Pro Asp Ile Met Ile Val His Gly Asp Arg Phe Asp Ala Leu Ala
            100                 105                 110

Leu Ala Thr Ser Ala Ala Leu Met Asn Ile Arg Ile Leu His Ile Glu
            115                 120                 125

Gly Gly Glu Val Ser Gly Thr Ile Asp Asp Ser Ile Arg His Ala Ile
    130                 135                 140

Thr Lys Leu Ala His Tyr His Val Cys Cys Thr Arg Ser Ala Glu Gln
145                 150                 155                 160

His Leu Ile Ser Met Cys Glu Asp His Asp Arg Ile Leu Leu Ala Gly
            165                 170                 175

Cys Pro Ser Tyr Asp Lys Leu Leu Ser Ala Lys Asn Lys Asp Tyr Met
            180                 185                 190

Ser Ile Ile Arg Met Trp Leu Gly Asp Asp Val Lys Ser Lys Asp Tyr
            195                 200                 205

Ile Val Ala Leu Gln His Pro Val Thr Thr Asp Ile Lys His Ser Ile
    210                 215                 220

Lys Met Phe Glu Leu Thr Leu Asp Ala Leu Ile Ser Phe Asn Lys Arg
225                 230                 235                 240

Thr Leu Val Leu Phe Pro Asn Ile Asp Ala Gly Ser Lys Glu Met Val
            245                 250                 255

Arg Val Met Arg Lys Lys Gly Ile Glu His His Pro Asn Phe Arg Ala
            260                 265                 270
```

```
Val Lys His Val Pro Phe Asp Gln Phe Ile Gln Leu Val Ala His Ala
        275                 280                 285

Gly Cys Met Ile Gly Asn Ser Ser Cys Gly Val Arg Glu Val Gly Ala
        290                 295                 300

Phe Gly Thr Pro Val Ile Asn Leu Gly Thr Arg Gln Ile Gly Arg Glu
305                 310                 315                 320

Thr Gly Glu Asn Val Leu His Val Arg Asp Ala Asp Thr Gln Asp Lys
                325                 330                 335

Ile Leu Gln Ala Leu His Leu Gln Phe Gly Lys Gln Tyr Pro Cys Ser
                340                 345                 350

Lys Ile Tyr Gly Asp Gly Asn Ala Val Pro Arg Ile Leu Lys Phe Leu
                355                 360                 365

Lys Ser Ile Asp Leu Gln Glu Pro Leu Gln Lys Phe Cys Phe Pro
        370                 375                 380

Pro Val Lys Glu Asn Ile Ser Gln Asp Ile Asp His Ile Leu Glu Thr
385                 390                 395                 400

Leu Ser Ala Leu Ala Val Asp Leu Gly Gly Thr Asn Leu Arg Val Ala
                405                 410                 415

Ile Val Ser Met Lys Gly Glu Ile Val Lys Lys Tyr Thr Gln Phe Asn
                420                 425                 430

Pro Lys Thr Tyr Glu Glu Arg Ile Asn Leu Ile Leu Gln Met Cys Val
        435                 440                 445

Glu Ala Ala Ala Glu Ala Val Lys Leu Asn Cys Arg Ile Leu Gly Val
        450                 455                 460

Gly Ile Ser Thr Gly Gly Arg Val Asn Pro Arg Glu Gly Ile Val Leu
465                 470                 475                 480

His Ser Thr Lys Leu Ile Gln Glu Trp Asn Ser Val Asp Leu Arg Thr
                485                 490                 495

Pro Leu Ser Asp Thr Leu His Leu Pro Val Trp Val Asp Asn Asp Gly
                500                 505                 510

Asn Cys Ala Ala Leu Ala Glu Arg Lys Phe Gly Gln Gly Lys Gly Leu
        515                 520                 525

Glu Asn Phe Val Thr Leu Ile Thr Gly Thr Gly Ile Gly Gly Gly Ile
        530                 535                 540

Ile His Gln His Glu Leu Ile His Gly Ser Ser Phe Cys Ala Ala Glu
545                 550                 555                 560

Leu Gly His Leu Val Val Ser Leu Asp Gly Pro Asp Cys Ser Cys Gly
                565                 570                 575

Ser His Gly Cys Ile Glu Ala Tyr Ala Ser Gly Met Ala Leu Gln Arg
                580                 585                 590

Glu Ala Lys Lys Leu His Asp Glu Asp Leu Leu Leu Val Glu Gly Met
        595                 600                 605

Ser Val Pro Lys Asp Glu Ala Val Gly Ala Leu His Leu Ile Gln Ala
        610                 615                 620

Ala Lys Leu Gly Asn Ala Lys Ala Gln Ser Ile Leu Arg Thr Ala Gly
625                 630                 635                 640

Thr Ala Leu Gly Leu Gly Val Val Asn Ile Leu His Thr Met Asn Pro
                645                 650                 655

Ser Leu Val Ile Leu Ser Gly Val Leu Ala Ser His Tyr Ile His Ile
                660                 665                 670

Val Lys Asp Val Ile Arg Gln Gln Ala Leu Ser Ser Val Gln Asp Val
        675                 680                 685
```

-continued

```
Asp Val Val Val Ser Asp Leu Val Asp Pro Ala Leu Leu Gly Ala Ala
    690             695             700
Ser Met Val Leu Asp Tyr Thr Thr Arg Arg Ile Tyr
705             710             715
```

METHODS AND COMPOSITIONS FOR MODULATING SIALIC ACID PRODUCTION AND TREATING HEREDITARY INCLUSION BODY MYOPATHY

CROSS-REFERENCE TO RELATED APPLICATIONS

This application claims priority to, and incorporates by reference, U.S. provisional patent application Ser. No. 60/900,034, filed Feb. 7, 2007.

FIELD OF THE INVENTION

The field of the present invention relates to methods and compositions for modulating sialic acid production in a system. The field of the present invention further relates to methods and compositions for treating and/or preventing Hereditary Inclusion Body Myopathy and/or symptoms thereof.

BACKGROUND OF THE INVENTION

Hereditary Inclusion Body Myopathy (HIBM2) is a chronic progressive skeletal muscle wasting disorder, which generally leads to complete disability before the age of 50 years. There is currently no effective therapeutic treatment for HIBM2. Development of this disease is related to expression in family members of an autosomal recessive mutation of the GNE gene, which encodes the bifunctional enzyme UDP-GlcNAc 2-epimerase/ManNAc kinase (GNE/MNK). This is the rate-limiting bifunctional enzyme that catalyzes the first 2 steps of sialic acid biosynthesis. Decreased sialic acid production consequently leads to decreased sialyation of a variety of glycoproteins, including the critical muscle protein alpha-dystroglycan ($\alpha$-DG). This in turn severely cripples muscle function and leads to the onset of the syndrome.

SUMMARY OF THE INVENTION

According to certain embodiments of the present invention, methods for modulating the production of sialic acid in a system are provided, which comprise providing the system with a wild-type GNE-encoding nucleic acid sequence. According to such embodiments, the system may comprise a cell, muscular tissue, or other desirable targets. Similarly, the present invention encompasses methods for introducing and expressing wild-type GNE in a system that comprises a mutated endogenous GNE-encoding sequence. In other words, the present invention includes providing, for example, a cell or muscular tissue that harbors a mutated (defective) GNE-encoding sequence with a functional wild-type GNE encoding sequence.

According to additional embodiments of the present invention, methods for treating, preventing, and/or ameliorating the effects of Hereditary Inclusion Body Myopathy are provided. Such methods generally comprise providing a patient with a wild-type GNE-encoding nucleic acid sequence. The wild-type GNE-encoding nucleic acid sequence may, optionally, be delivered to a patient in connection with a lipid nanoparticle, either via muscular injection or intravenous administration.

According to yet further embodiments of the invention, novel compositions are provided for expressing wild-type GNE in a system. The compositions preferably include a wild-type GNE-encoding nucleic acid sequence disposed within or connected to a lipid nanoparticle. The lipid nanoparticle may, optionally, be decorated with agents that are capable of recognizing and binding to muscle cells, muscle tissue, or components of the foregoing.

BRIEF DESCRIPTION OF THE FIGURES

The file of this patent application contains at least one drawing executed in color. Copies of this patent with color drawing(s) will be provided by the United States Patent and Trademark Office upon request and payment of the necessary fee.

FIG. 7: is a table that summarizes the toxicological studies described herein involving intramuscular injections of GMP DNA complexes.

FIG. 8: is a table that summarizes the toxicological studies described herein involving intravenous injections of GMP DNA complexes.

FIG. 14: is an image of a gel showing GNE mRNA derived from mice injected with the GNE-encoding sequences described herein.

BRIEF DESCRIPTION OF THE SEQUENCE LISTING

SEQ ID NO: 1-6 are the nucleic acid sequences of the PCR primers listed in Table-1 below.

SEQ ID NO: 7-8 are GNE-specific PCR primers.

Figure 1:
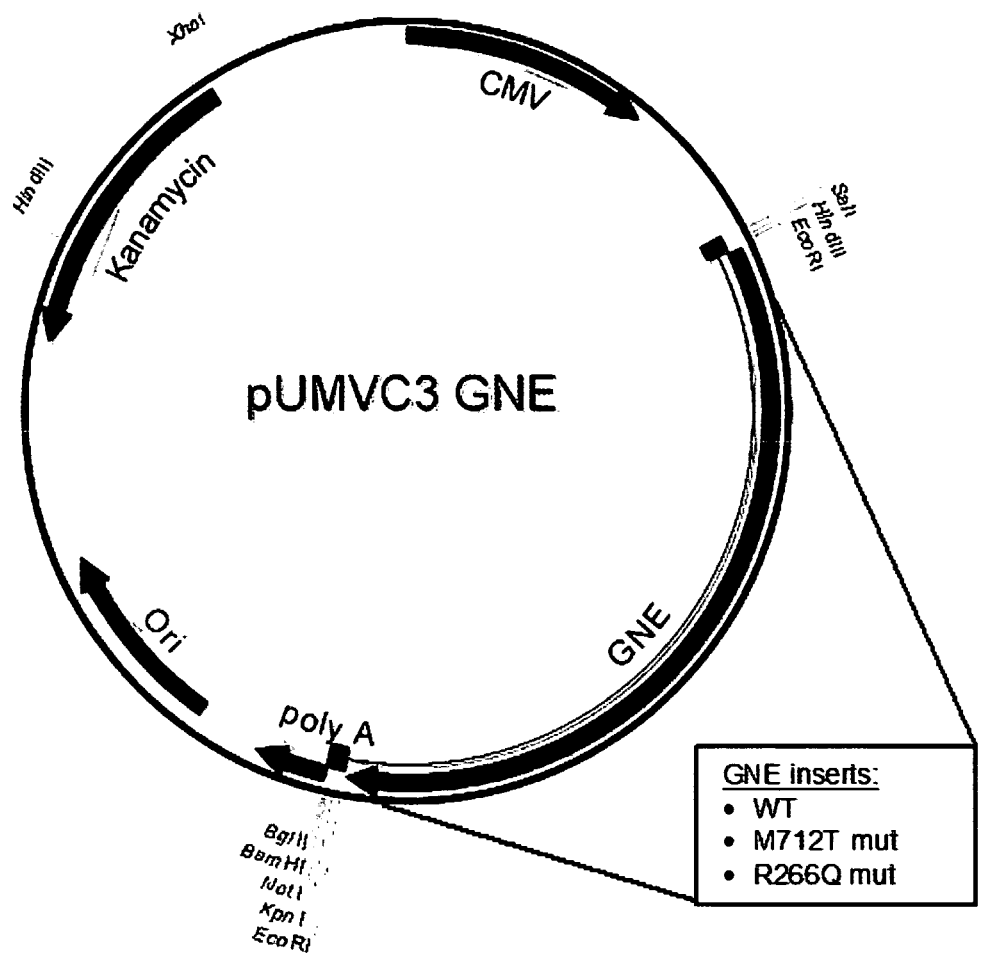
FIG. 1: is a diagram of the pUMVC3-GNE expression vector described herein.

SEQ ID NO: 9 is the nucleic acid sequence of the PUMVC3-wt-DNA construct described herein and shown in FIG. 1.

SEQ ID NO: 10 is the GNE-encoding sequence contained within the PUMVC3-wt-DNA construct.

SEQ ID NO: 11 is the wild-type amino acid sequence of GNE.

SEQ ID NO: 12 is the modified nucleic acid sequence for GNE-R266Q.

SEQ ID NO: 13 is the modified amino acid sequence for GNE-R266Q.

SEQ ID NO: 14 is the mutated nucleic acid sequence for GNE-M712T (a mutation that causes HIBM2).

SEQ ID NO: 15 is the mutated amino acid sequence for GNE-M712T (a mutation that causes HIBM2).

SEQ ID NO: 16 is the wild-type amino acid sequence of GNE.

DETAILED DESCRIPTION OF THE INVENTION

According to certain embodiments of the present invention, methods for modulating the production of sialic acid in a system are provided. The methods generally comprise providing the system with a wild-type GNE-encoding nucleic acid sequence. The wild-type GNE-encoding nucleic acid sequence may, preferably, comprise a promoter operably connected thereto. The promoter will preferably be functional and capable of driving the expression of the GNE-encoding nucleic acid sequence in the target cell (or target extra-cellular space). A non-limiting example of a promoter that may be operably connected to a GNE-encoding sequence is the CMV promoter, which is shown to be operably connected to the wild-type GNE-encoding nucleic acid sequence of the PUMVC3-wt-DNA construct (FIG. 1).

As used herein, the terms "GNE-encoding nucleic acid sequence," "wild-type GNE-encoding sequence," "GNE-encoding sequence," and similar terms refer to a nucleic acid sequence that encodes the wild-type bifunctional enzyme UDP-GlcNAc 2-epimerase/ManNAc kinase (GNE/MNK), which is represented by the amino acid sequence of SEQ ID NO: 11. A GNE-encoding sequence may only include a nucleic acid sequence that encodes the wild-type form of GNE, such as SEQ ID NO: 10. Alternatively, the GNE-encoding sequence may comprise the nucleic acid sequence that encodes the wild-type form of GNE, along with other transcriptional control elements, such as a promoter, termination sequence, and/or other elements. A non-limiting example of such a GNE-encoding sequence is the pUMVC3 GNE construct shown in FIG. 1, which consists of the nucleic acid sequence of SEQ ID NO: 9.

The terms "GNE-encoding nucleic acid sequence," "wild-type GNE-encoding sequence," "GNE-encoding sequence," and similar terms are further meant to include a nucleic acid sequence which, by virtue of the degeneracy of the genetic code, is not identical with that shown in any of the sequences shown in the Sequence Listing appended hereto, but which still encodes the amino acid sequence of the wild-type GNE (SEQ ID NO: 11), or a modified nucleic acid sequence that encodes a different amino acid sequence, provided that the resulting GNE protein retains substantially the same (or even an improved) activity of the wild-type GNE protein. A non-limiting example of such a modified GNE protein includes the GNE isoform R266Q described herein (SEQ ID NO: 13). That is, modifications to a GNE-encoding sequence that alter the amino acid sequence of the wild-type GNE protein in such a way that one amino acid is replaced with a similar amino acid are encompassed by the present invention, as well as other modifications which do not substantially negatively affect GNE activity because the change (whether it be substitution, deletion or insertion) does not negatively affect the active site of the GNE protein.

As used herein, the term "system" refers to any biological system that is capable of receiving a GNE-encoding sequence described herein, including any type of cell or biological organism. In addition, a "system" may further include an intercellular space within a biological organism.

According to certain embodiments of the invention, the GNE-encoding sequence may be disposed in or connected to an appropriate carrier or delivery vehicle. Various strategies may be employed to deliver the GNE-encoding sequences described herein into target cells, including the use of lipid carriers (lipid nanoparticles), viral vectors, biodegradable polymers, polymer microspheres (e.g., 50 nm or smaller), and various conjugate systems and related cytofectins.

The use of liposomes or other particle forming compositions is a preferred delivery vehicle for the GNE-encoding sequences described herein. Liposomes are attractive carriers insofar as they protect biological molecules, such as the GNE-encoding sequences described herein, from degradation while improving cellular uptake. One of the most commonly used classes of liposome formulations for delivering polyanions (e.g., DNA) is that which contains cationic lipids.

Lipid aggregates may be formed with macromolecules using cationic lipids alone or including other lipids and amphiphiles, such as phosphatidylethanolamine. It is well-known in the art that both the composition of the lipid formulation, as well as its method of preparation, have an effect on the structure and size of the resultant anionic macromolecule-cationic lipid aggregate. These factors can be modulated to optimize delivery of polyanions to specific cell types in vitro and in vivo.

The use of cationic lipids for cellular delivery of the GNE-encoding compositions described herein has several advantages. The encapsulation of anionic compositions using cationic lipids is essentially quantitative due to electrostatic interaction. In addition, it is believed that the cationic lipids interact with the negatively charged cell membranes, thereby initiating cellular membrane transport.

Experiments have shown that plasmid DNA may be encapsulated in small particles, which generally consist of a single plasmid encapsulated within a bilayer lipid vesicle (Wheeler, et al., 1999, Gene Therapy 6, 271-281). These particles often contain the fusogenic lipid dioleoylphosphatidylethanolamine (DOPE), low levels of a cationic lipid, and can be stabilized in aqueous media by the presence of a poly(ethylene glycol) (PEG) coating.

These lipid particles have systemic applications, as they exhibit extended circulation lifetimes following intravenous (i.v.) injection, can accumulate preferentially in various tissues and organs due to the enhanced vascular permeability in such regions, and can be designed to escape the lysomic pathway of endocytosis by disruption of endosomal membranes. These properties can be useful in delivering biologically active molecules, such as GNE-encoding sequences, to various cell types for experimental and therapeutic applications, such as to muscle tissue cells. Various lipid nucleic acid particles and methods of preparation thereof are described in U.S. Patent Application Publication Nos. 2008-0020058, 2003-0077829, 2003-0108886, 2006-0051405, 2006-0083780, 2003-0104044, 2006-0051405, 2004-0142025, 2006-00837880, 2005-0064595, 2005-0175682, 2005-0118253, 2005-0255153 and 2005-0008689; and U.S. Pat. Nos. 5,885,613; 6,586,001; 6,858,225; 6,858,224; 6,815,432; 6,586,410; 6,534,484; and 6,287,591, all of which are incorporated herein by reference in their entirety.

The invention provides that the GNE-encoding sequences, and/or the associated delivery vehicles used therewith, may be targeted towards specific cell types, for example, muscle cells, muscle tissue, and the like. For example, the liposomal nanoparticles can be directed to bind to cell surfaces by a number of specific interactions. This binding facilitates the uptake of the DNA into the cell by one of several well understood cell entry pathways. Rapid sequestration of the nanoparticles (e.g., liposomes) by these interactions reduces their time in the peripheral circulation, thereby decreasing the likelihood of degradation and nonspecific uptake. General targeting agents include, but are not limited to, transferrin (Trf) which binds to the transferrin receptor (TrfR) on a cell surface—or using an antibody (or a derivative thereof) that binds to the TrfR on the cell surface. Muscle has a relatively high proportion of TrfR on its cell surfaces. Another target for sequestration is the epidermal growth factor receptor (EGFR), which is prevalent on the surface of muscle cells and other epitheleoid cell types. Erbitux (an EGFR monoclonal antibody approved for human use) is an exemplary agent for EGFR-targeting, which may also be used to decorate the liposomal nanoparticles described herein. Additional targeting moieties can be, but are not limited to, lectins or small molecules (peptides or carbohydrates) which recognize and bind to specific targets found only on (or are more restricted to) muscle cells. The advantage of smaller (and possibly higher affinity) molecules is that they could be present at a higher density on the surface of the nanoparticles employed.

The GNE-encoding sequences described herein, which preferably are used and delivered to a system in connection with an appropriate delivery vehicle (such as a liposome or lipid nanoparticle), may be administered to a system using any of various well-know techniques. For example, in the case of a mammal, the GNE-encoding sequences may be administered to a mammal via parenteral injection. The term "parenteral," as used herein, includes subcutaneous, intracutaneous, intravenous, intramuscular, intraarticular, intraarterial, intrasynovial, or infusion techniques.

The GNE-encoding sequences and related compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated composition or its delivery form. For example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid may be used in the preparation of injectables.

According to certain embodiments, a Plasma-Lyte® carrier may be employed and used to deliver a GNE-encoding sequence, particularly for parenteral injection. (Baxter Laboratories, Inc., Morton Grove, Ill.). Plasma-Lyte® is a sterile, non-pyrogenic isotonic solution that may be used for intravenous administration. Each 100 mL volume contains 526 mg of Sodium Chloride, USP (NaCl); 502 mg of Sodium Gluconate ($C_6H_{11}NaO_7$); 368 mg of Sodium Acetate Trihydrate, USP ($C_2H_3NaO_2.3H_2O$); 37 mg of Potassium Chloride, USP (KCl); and 30 mg of Magnesium Chloride, USP ($MgCl_2.6H_2O$). It contains no antimicrobial agents. The pH is preferably adjusted with sodium hydroxide to about 7.4 (6.5 to 8.0).

The injectable formulations used to deliver GNE-encoding sequences may be sterilized, for example, by filtration through a bacterial-retaining filter, or by incorporating sterilizing agents in the form of sterile solid compositions, which can be dissolved or dispersed in sterile water, Plasma-Lyte® or other sterile injectable medium prior to use.

In order to prolong the expression of a GNE-encoding sequence within a system (or to prolong the effect thereof), it may be desirable to slow the absorption of the composition from subcutaneous or intramuscular injection. This may be accomplished by the use of a liquid suspension of crystalline or amorphous material with poor water solubility. The rate of absorption of the composition may then depend upon its rate of dissolution, which, in turn, may depend upon crystal size and crystalline form.

Alternatively, delayed absorption of a parenterally administered GNE-encoding sequence may be accomplished by dissolving or suspending the composition in an oil vehicle. Injectable depot forms may be prepared by forming microencapsule matrices of the GNE-encoding sequence in biodegradable polymers such as polylactide-polyglycolide. Depending upon the ratio of GNE-encoding sequence material to polymer and the nature of the particular polymer employed, the rate of GNE-encoding sequence release can be controlled. Examples of other biodegradable polymers include poly(orthoesters) and poly(anhydrides). As described above, depot injectable formulations may also be prepared by entrapping the GNE-encoding sequence in liposomes (or even microemulsions) that are compatible with the target body tissues, such as muscular tissue.

In addition to methods for modulating the production of sialic acid in a system, the present invention further encompasses methods for producing wild-type GNE in a system. According to such embodiments, the system (e.g., the muscle cells of a human patient) may comprise a mutated endogenous GNE-encoding sequence (e.g., the GNE-M712T sequence of SEQ ID NO: 14). In other words, the present invention includes providing, for example, a cell or muscular tissue that harbors a mutated (defective) GNE-encoding sequence with a functional wild-type GNE encoding sequence. The wild-type GNE encoding sequence may be delivered to such a system using, for example, the liposomes or lipid nanoparticles described herein, via parenteral injection.

According to additional related embodiments of the present invention, methods for treating, preventing, and/or ameliorating the effects of Hereditary Inclusion Body Myopathy (HIBM2) are provided. Such methods generally comprise providing a patient with a therapeutically effective amount of a wild-type GNE-encoding nucleic acid sequence. In certain embodiments, the wild-type GNE-encoding nucleic acid sequence may, preferably, be delivered to a patient in connection with a lipid nanoparticle and a carrier similar to that of Plasma-Lyte®, via parenteral injection.

The phrase "therapeutically effective amount" of a wild-type GNE-encoding nucleic acid sequence refers to a sufficient amount of the sequence to express sufficient levels of wild-type GNE, at a reasonable benefit-to-risk ratio, to increase sialic acid production in the targeted cells and/or to otherwise treat, prevent, and/or ameliorate the effects of HIBM2 in a patient. It will be understood, however, that the total daily usage of the wild-type GNE-encoding nucleic acid sequence and related compositions of the present invention will be decided by the attending physician, within the scope of sound medical judgment.

The specific therapeutically effective dose level for any particular patient may depend upon a variety of factors, including the severity of a patient's HIBM2 disorder; the activity of the specific GNE-encoding sequence employed; the delivery vehicle employed; the age, body weight, general health, gender and diet of the patient; the time of administration, route of administration, and rate of excretion of the specific GNE-encoding sequence employed; the duration of the treatment; drugs used in combination or contemporaneously with the specific GNE-encoding sequence employed; and like factors well-known in the medical arts.

Upon improvement of a patient's condition, a maintenance dose of a GNE-encoding sequence may be administered, if necessary. Subsequently, the dosage or frequency of administration, or both, may be reduced, as a function of the symptoms, to a level at which the improved condition is retained when the symptoms have been alleviated to the desired level.

According to yet further embodiments of the invention, novel compositions are provided for expressing wild-type GNE in a system. The compositions preferably include a wild-type GNE-encoding nucleic acid sequence. As described herein, the GNE-encoding nucleic acid sequence may comprise various transcriptional control elements, such as a promoter, termination sequence, and others. A non-limiting example of a composition encompassed by the present invention includes the pUMVC3-GNE expression vector described herein, shown in FIG. 1, and represented by SEQ ID NO: 9. Also as described relative to other embodiments of the present invention, the GNE-encoding nucleic acid sequence may be disposed within or connected to an appropriate vehicle for delivery to a system, such as a liposome or lipid nanoparticle. Still further, according to such embodiments, the delivery vehicle may, optionally, be decorated with agents that are capable of recognizing and binding to target cells or tissues, such as muscle cells or muscle tissues.

EXAMPLES

Example 1

Expression of Exogenous GNE in CHO-Lec3 Cells

In the following example, several GNE expression vectors from human cDNA were created. Three different GNE forms, wild type, M712T, and R266Q, were robustly expressed in GNE deficient cells (Lec3 cells). All enzymes demonstrated similar protein expression levels, albeit distinct enzymatic activities. As the following will show, the transfected GNE expressing cell lines produced significantly more sialic acid than untransfected cells.

Example 1 Methodology.

GNE Cloning. Parental vectors containing the GNE cDNA were provided by Daniel Darvish (HIBM Research Group, Encino, Calif.) and included pGNE-NB8 (wild type), pGNE-MB18 (M712T mutant), and pGNE-R266Q (R266Q mutant). The destination vector, pUMVC3, was purchased from Aldevron (Fargo, N. Dak.). The subcloning vector, pDrive (Qiagen, Valencia, Calif.), was used to shuttle the R266Q mutant from the parent vector to the destination vector.

Wild type and M712T GNE was cloned from the parent vector into pUMVC3 via Eco RI restriction digest, gel purification, and T4 ligation. The R266Q mutant GNE was cloned from the parent vector into pDrive via Hind III+Xba I digest and then moved to pUMVC3 via Sal I+Xba I. (FIG. 1). All pUMVC3-GNE clones were sequenced by Seqwright (Houston, Tex.) with the primers set forth in the Table-1 below.

TABLE 1

| | | |
|---|---|---|
| GNE-F1 | 5'-TGTGAGGACCATGATCGCATCCTT-3' | SEQ ID NO: 1 |
| GNE-F2 | 5'-ACCTCCGAGTTGCAATAGTCAGCA-3' | SEQ ID NO: 2 |
| GNE-R1 | 5'-AATCAGGCCCATCCAGAGACACAA-3' | SEQ ID NO: 3 |
| GNE-R2 | 5'-TTCCAATCTGACGTGTTCCCAGGT-3' | SEQ ID NO: 4 |
| UMVC-F | 5'-CGCCACCAGACATAATAGCTGACA-3' | SEQ ID NO: 5 |
| UMVC-R | 5'-TAGCCAGAAGTCAGATGCTCAAGG-3' | SEQ ID NO: 6 |

Positive pUMVC3-GNE clones were grown overnight in 175 mls LB broth+50 µg/ml Kan and 150 mls culture was used for a Qiagen (Valencia, Calif.) HiSpeed Plasmid Maxi kit according to the manufacturer protocols.

DNA:lipid complex. The DNA:lipid complex used in this example was produced by mixing, at room temperature, 1,2-Dioleoyl-3-Trimethylammonium-Propane (DOTAP) with test DNA (pUMVC3-GNE). DOTAP is a commercially-available lipid particle that is offered by Avanti Polar Lipids, Inc. (Alabaster, Ala.). The DOTAP was mixed with the pUMVC3-GNE DNA in a manner to achieve the desired total volume, which exhibited a final ratio of 0.5 µg DNA:4 mM DOTAP, in a final volume of 1 µl.

Cell Culture. GNE-deficient CHO-Lec3 cells were provided by Albert Einstein College of Medicine. The cells were grown at 37° C. in 5% $CO_2$ in alpha-MEM media supplemented with 4 mM L-glutamine and 10% heat inactivated, Fetal Bovine Serum. Cells for transient transfections were plated at $1\times10^6$ cells per well in 6-well plates and grown overnight. Lec3 cells were weaned to reduced serum conditions by reducing the FBS by 2.5% per passage.

Transient Transfections. Lec3 cells were transfected for 6 hours with DNA:lipid complex per well in OptiMEM (Invitrogen, Carlsbad Calif.), then the media was changed to normal alpha-MEM growth media and the cells were cultured overnight. DNA:lipid complexes were formed by mixing 4 µg DNA+10 µl Lipofectamine 2000 (Invitrogen) according to the manufacturers protocol. Twenty-four hours post-transfection, cells were harvested by trypsin digest and washed once with PBS before subsequent western blot or enzyme/sugar assays.

mRNA Quantitation. Total RNA was extracted from 1.5 million transfected CHO-Lec3 cells using the RNeasy kit according to the manufacturers instructions (Qiagen, Valencia, Calif.). The purified RNA was quantified by 260/280 ratio using a NanoDrop1000 spectrophotometer (NanoDrop, Wilmington, Del.). Five hundred nanograms of total RNA was converted to cDNA using oligo dT primers and the TaqMan reverse transcription kit (ABI, Foster City, Calif.). Using the Sybr Green PCR master mix (ABI, Foster City, Calif.) along with 25 ng cDNA and 0.2 pM primers (GNE-F3=5'- cggaagaagggcattgagcatc-3' (SEQ ID NO: 7) and GNE-R3=5'-tttgtcttgggtgtcagcatcc-3' (SEQ ID NO: 8)), 25 µl PCR reactions were compared against serial dilutions of a known concentration of pUMVC3GNE-wt DNA. The Sybr Green fluorescence was detected using the iQ5 real-time PCR detection system (BioRad, Hercules, Calif.) and the PCR conditions: 95° C.—10 minutes to activate the enzyme and (95° C.—15 seconds and 58° C.—60 seconds)×45 cycles to amplify the product. Fifteen microliters of the PCR reaction was run on a 4% pre-cast agarose E-gel (Invitrogen, Carlsbad, Calif.) and the image was captured using the G-box chemiluminescence detection system (Frederick, Md.).

Western Blot. Approximately $5 \times 10^5$ cells were used for Western blot analysis. Cell pellets were lysed using 20 µl Cell lytic (Sigma, St. Louis, Mo.), plus 1% protease inhibitors. The cell debris were spun down at maximum speed for 5 minutes and the supernatant was mixed 1:1 with Laemmli buffer (BioRad, Hercules, Calif.) containing 5% β-ME. Protein samples were separated by polyacrylamide electrophoresis at 100V for 2 hours on 10% denaturing gels, followed by transfer to a PVDF membrane using 100 volts for 2 hours. The membranes were probed for GNE and GapDH using chicken anti-GNE (1:10,000 dilution) and mouse anti-GapDH (1:50,000 dilution) overnight. Primary antibodies were detected using HRP-labeled secondary antibodies and they were visualized using the West Dura detection reagent (Pierce, Rockford, Ill.) and the G-box chemiluminescence camera (Syngene, Frederick, Md.).

Sialic Acid Quantitation. Approximately $4 \times 10^6$ cells were used for the quantification of membrane-bound sialic acid by the thiobarbituric acid method. Cells were resuspended in water and lysed by passage through a 25 gauge needle 20 times and centrifuged. The supernatant was used for Bradford protein estimation and the remaining pellet was resuspended in 100 µl 2M acetic acid and incubated for 1 hour at 80° C. to release glycoconjugate-bound sialic acids. 137 µl of periodic acid solution (2.5 mg/ml in 57 mM $H_2SO_4$) were added and incubated for 15 minutes at 37° C. Next, 50 µl of sodium arsenite solution (25 mg/ml in 0.5 M HCl) were added and the tubes were shaken vigorously to ensure complete elimination of the yellow-brown color. Following this step, 100 µl of 2-thiobarbituric acid solution (71 mg/ml adjusted to pH 9.0 with NaOH) were added and the samples were heated to 100° C. for 7.5 minutes. The solution was extracted with 1 ml of butanol/5% 12M HCl and the phases were separated by centrifugation. The absorbance of the organic phase was measured at 549 nm. The amount of sialic acid was measured as nmol sialic acid/mg of protein.

Kinase and Epimerase Activity. UDP-GlcNAc 2-epimerase activity was determined by a colorimetric assay. It contained 45 mM $Na_2HPO_4$, pH 7.5, 10 mM $MgCl_2$, 1 mM UDP-GlcNAc and variable amounts of protein in a final volume of 200 µl. The reaction was performed at 37° C. for 30 minutes and stopped by boiling for 1 minute. The released ManNAc was detected using the Morgan-Elson method. In brief, 150 µl of sample were mixed with 30 µl of 0.8 M $H_3BO_3$, pH 9.1, and boiled for 3 minute. Next, 800 µl of DMAB solution (1% (w/v) 4-dimethylamino benzaldehyde in acetic acid/1.25% 10N HCl) was added and incubated at 37° C. for 30 minutes. The absorbance was read at 578 nm.

ManNAc kinase activity was measured by a radiometric assay. It contained 60 mM Tris/HCl, pH 8.1, 10 mM $MgCl_2$, 5 mM ManNAc, 50 nCi [$^{14}$C]ManNAc, 10 mM ATP, and variable amounts of protein in a final volume of 200 µl. The reaction was performed at 37° C. for 30 minutes and stopped by addition of 300 µl of ethanol. Radio-labeled compounds were separated by paper chromatography and radioactivity was determined by liquid scintillation counting.

Statistical Analysis. Three independent experiments for enzyme activity and sialic acid expression were performed. The average and standard deviation was calculated using Microsoft Excel. A student's t-test was used to determine p-values for each treated group, relative to the untreated sample.

Example 1 Results.

Figure 2:
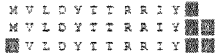
FIG. 2: is a diagram that shows a sequence alignment of NM_005467, (SEQ ID NO: 11 with GNE wt (NB8), (SEQ ID NO: 16); M712T (MB18), (SEQ ID NO: 15); and R266Q (R266Q)(SEQ ID NO: 13). The original DNA sequence was converted into an amino acid sequence to illustrate the mutations located therein.

GNE clones. The GNE cDNA clones that were tested included a human wild type cDNA and two human mutant cDNAs. The mutants included the M712T GNE deficient clone and the R266Q sialuria clone. Sialuria is a human disease caused by point mutations in the CMP-sialic acid binding site of GNE, leading to a loss of feed-back inhibition and mass production of sialic acids. GNE cDNAs were subcloned from their original vectors to the expression vector, pUMVC3, by restriction digest cloning. Clones were screened by directional restriction enzyme digest to confirm the GNE insert was in the correct orientation. Positive clones were sequenced in both orientations to confirm that no mutations occurred during the cloning process. The resulting chromatograms were compared against the GNE sequence from GenBank (accession # NM_005467) and the wild type did not exhibit any mutations, while the M712T and R266Q clones contained only the expected point mutations (FIG. 2). Positive pUMVC3-GNE clones were scaled using a maxi prep plasmid purification procedure and sequenced again to confirm that no mutations occurred. These DNA stocks were used for all subsequent experiments.

Figure 3:
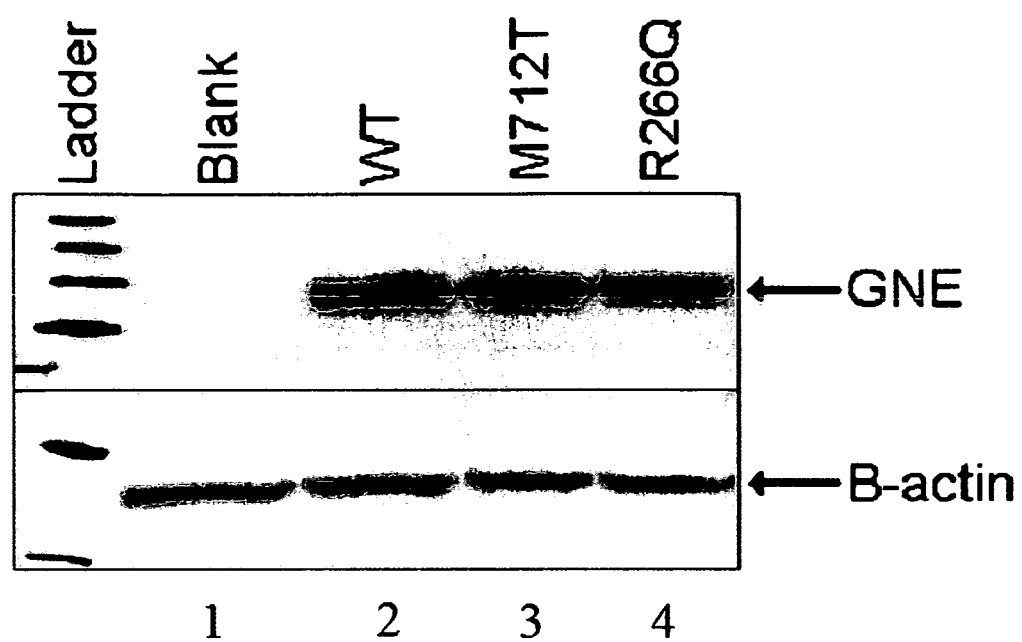
FIG. 3: is an image of a gel that shows GNE expression in CHO-Lec3 cells grown in 10% serum. Lane 1: untreated Lec3 cells. Lane 2: wt GNE. Lane 3: M712T GNE. Lane 4: R266Q GNE.
Figure 4:
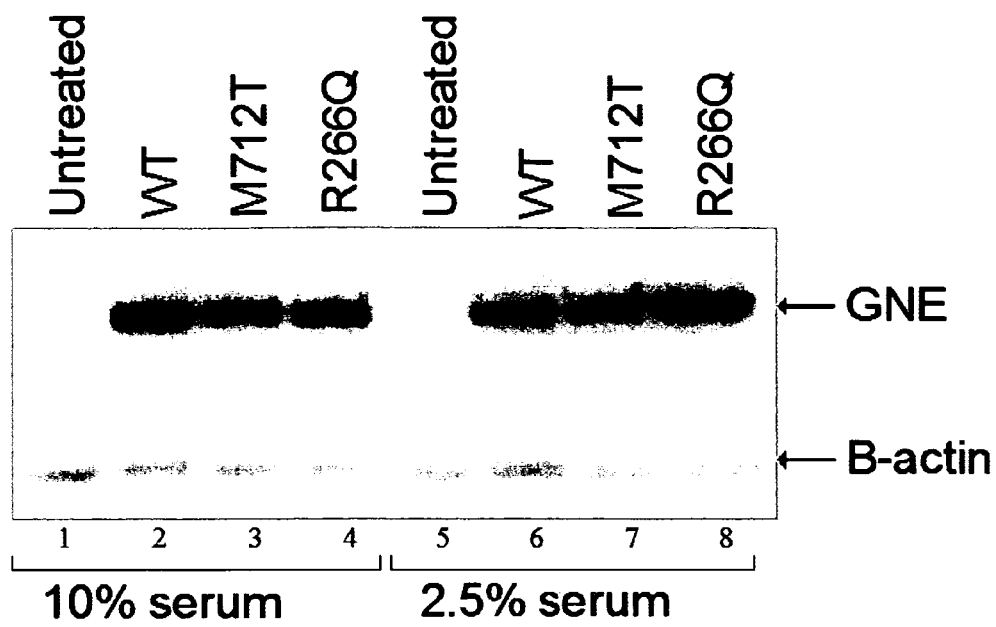
FIG. 4: is an image of a Western blot that shows GNE expression in CHO-Lec3 cell lines. Lanes 1-4: CHO-Lec3 cells grown in 10% FBS. Lanes 5-8: CHO-Lec3 cells grown in 2.5% FBS. Lanes 1 and 5: Untreated Lec3 cells. Lanes 2 and 6: wt GNE. Lanes 3 and 7: M712T GNE. Lanes 4 and 8: R266Q GNE.

Gene protein expression. Plasmid UMVC3-GNE DNA was transiently transfected into CHO-Lec3 cells and grown in 10% serum for 24 hours, and then the cells were harvested and analyzed for recombinant GNE expression. A GNE Western blot illustrated that the untreated Lec3 cells (which were not transfected) do not express GNE and CHO-Lec3 cells transfected with different pUMVC3 clones express high levels of recombinant GNE (FIG. 3). The expression level was relatively equivalent, regardless of GNE isoform. In a second experiment, recombinant GNE was expressed following transfection of CHO-Lec3 cells grown in 10% or 2.5% fetal bovine serum (FBS), due to the ability of CHO cells to incorporate sialic acids from the culture media. Again, GNE protein expression was relatively equivalent, regardless of GNE isoform and the concentration of FBS (FIG. 4).

Figure 5:
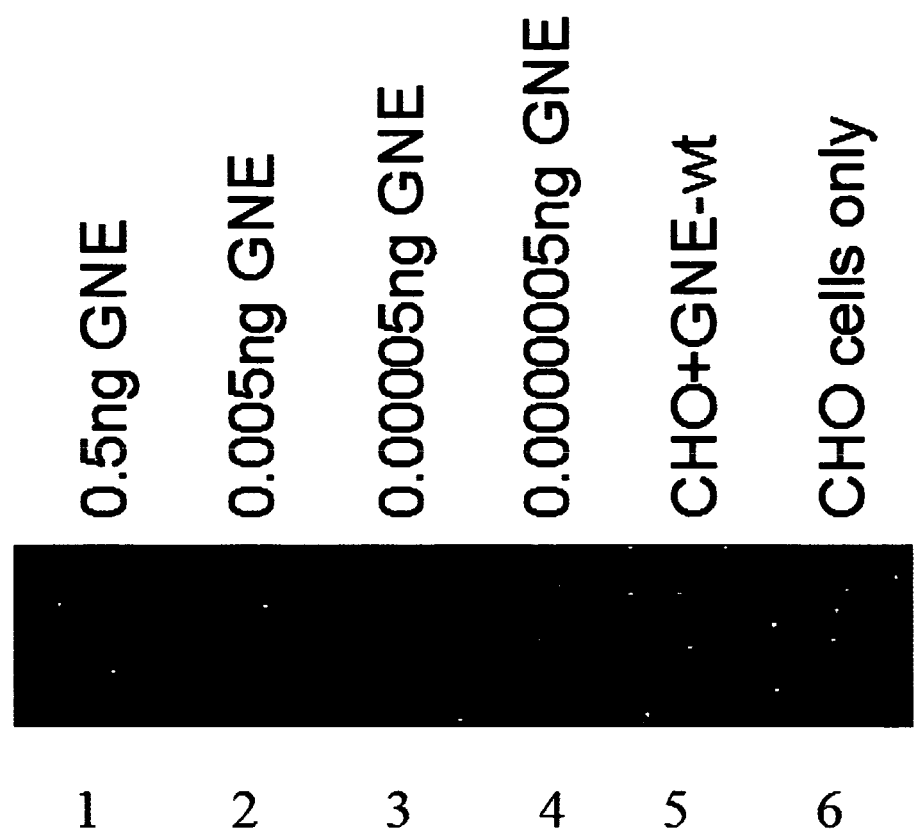
FIG. 5: is an image of a gel that shows GNE mRNA is expressed in transfected CHO-Lec3 cells, but not in control cells. Lanes 1-4 contain 15 µl of serial diluted pUMVC3-GNE-wt PCR product, which was used to quantitate the amount of GNE mRNA present in the Lec3 samples. Lanes 5-6 contain 15 µl of the PCR product from transfected or untransfected Lec3 cells.

Wt-GNE mRNA quantitation. CHO-Lec3 cells were grown in 10% serum and transiently transfected with pUMVC3-GNE-wt DNA for 24 hours to quantitate the amount of recombinant GNE RNA that was expressed. Total RNA was extracted and RT-qPCR was performed to amplify a 230 by fragment from the GNE transcript. Serial dilutions of pUMVC3-GNE-wt were used to determine that the concentration of GNE-wt expressed in transfected Lec3 cells was equal to 4.1 pg/µl. The dynamic range of the qPCR was from 5 ng-5 fg and there was no GNE mRNA product detected in control (untransfected) CHO-Lec3 cells (the cT value for untransfected cells was greater than 42 cycles, which is less than 5 fg). Therefore, recombinant GNE mRNA expression was detected in transfected Lec3 cells, while untransfected cells had undetectable amounts of GNE mRNA. (FIG. 5).

GNE enzyme assays. In addition to the Western blot assay, an aliquot of the transfected cell pellets were assayed for enzyme activity. As shown in Table 2 below, both epimerase and kinase activity were quantified in Lec3 cells with or without recombinant GNE protein

TABLE 2

GNE enzyme activity of CHO Lec3 cells
transfected with different plasmids

| Lec3 Cells + DNA | Epimerase Act (mU/mg) | p-value | Kinase Act (mU/mg) | p-value |
|---|---|---|---|---|
| Untreated | 1 ± 0.7 | | 2 ± 1.4 | |
| WT GNE | 22 ± 0.2 | 0.0003* | 35 ± 0.7 | 0.0006* |
| M712T GNE | 31 ± 1.4 | 0.0007* | 37 ± 5.4 | 0.0063* |
| R266Q GNE | 26 ± 2.9 | 0.0035* | 33 ± 2.6 | 0.0023* |

*comparison to untreated

Lec3 cells alone had both epimerase and kinase activities less than 3 mU/mg, which displays background activity. Cells expressing wild type, M712T, or R266Q GNE had an average of 22, 31, and 26 mU/mg of epimerase activity, respectively. The same Lec3 samples displayed an average of 35, 37, and 33 mU/mg of kinase activity. All of the cells expressing recombinant GNE had enzyme activity significantly above the non-treated cells with a p-value≤0.006 for both epimerase and kinase activities. There was no statistical difference in enzyme activity between the three different GNE isoforms, with p-values ranging from 0.11-0.47.

Sialic acid assays. Transfected Lec3 cells also were tested for cell surface sialic acid expression. All Lec3 samples had approximately 6.0 nmol/mg membrane bound sialic acid, with the exception of Lec3 cells transfected with the R266Q GNE, which had a 1.5-fold higher amount. The R266Q mutant lacks the feed-back inhibition of GNE and is known to cause an overproduction of intracellular sialic acids. Lec3 cells seem to be undersialylated, and this could only be overcome by expression of the sialuria mutant and not by the about 100-fold overexpression of wild-type GNE compared to wild-type CHO cells.

No differences between wild type (wt) and M712T GNE were observed. This was likely due to the incorporation of sialic acids from the cell culture medium, as it is known that sialic acids from FBS can bypass the defective GNE pathway. In this case, differences between wild type and M712T could be masked by the bypass. Therefore, the cell culture conditions were altered by reducing the percent serum (FBS) in the media. As shown in Table-3 below, as the serum level was reduced, sialic acid production decreased, with a marked decrease demonstrated at 2.5% FBS.

TABLE 3

| % FBS | Sialic Acid (nmol/mg) | p-value |
|---|---|---|
| 10 | 8.05 ± 0.27 | |
| 5.0 | 7.26 ± 0.61 | 0.2996* |
| 2.5 | 4.69 ± 1.20 | 0.0096* |

*comparison to 10% FBS

Figure 6:
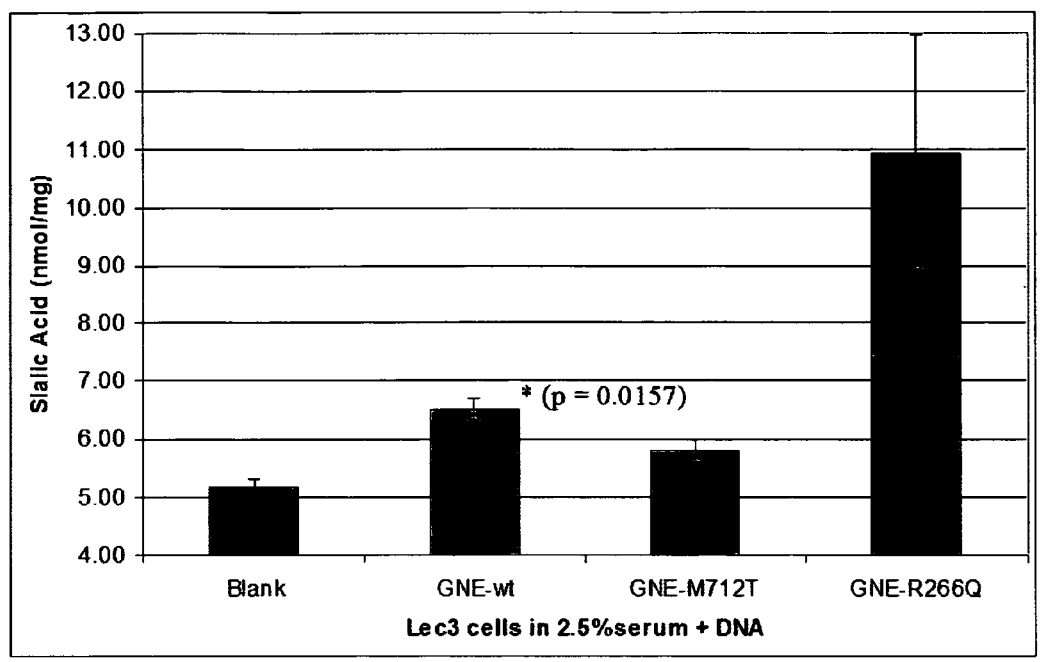
FIG. 6: is a bar graph that shows that sialic acid production is stimulated by GNE expression in CHO-Lec3 cells cultivated in the presence of 2.5% FBS. In comparison to untreated Lec3 cells ("blank"), sialic acid production was significant greater following GNE-wt (p=0.0157) transfection. GNE-R266Q (p=0.0566) and GNE-M712T (p=0.0708) approached significance.

Sialic acid levels continued to decrease as the cell culture media approached serum free conditions, but the cell morphology and growth characteristics were altered. It was determined that the 2.5% FBS concentration of the cell culture media was optimal in order to test the impact of GNE gene transfection in Lec3 cells. Lec3 cells were thus grown in 2.5% FBS and transfected with pUMVC3-GNE clones. GNE expression was concurrently confirmed via Western blot (FIG. 4). Significant increase of sialic acid production was indeed demonstrated, again with the best effect of the R226Q mutant (FIG. 6: p=0.0157 for GNE-wt; p=0.0566 for GNE R266Q). A slight, but significant; difference between wt and M712T GNE was observed, indicating that the re-sialylation capability of the mutant is lower than that of the wild-type, suggesting a similar mechanism in HIBM muscle.

Studies on HIBM2 reveal mutations in the GNE gene associated with glycosylation errors in the muscle membrane, which may lead to defective muscle function. Loss of GNE activity in HIBM2 is thought to impair sialic acid production and interfere with proper sialylation of glycoconjugates. The reactivities to lectins are also variable in some myofibers, suggesting that hyposialylation and abnormal glycosylation in muscles may contribute to the focal accumulations of autophagic vacuoles and/or amyloid deposits in affected patient muscle tissue. The foregoing example demonstrates the effect of a novel GNE gene/CMV promoter plasmid for mRNA and protein expression in GNE deficient CHO-Lec 3 cells, which were shown to be capable of restoring GNE/MNK enzyme function and subsequent induction of sialic acid production.

Example 2

Expression of Exogenous GNE In Vivo

The following example demonstrates the ability of the GNE-encoding sequences described herein to be transfected into live mice, and to stimulate GNE expression in the muscular tissue of such mice.

DNA:lipid complex. The materials used in this example included pUMVC3-wt-DNA (FIG. 1) and 1,2-Dioleoyl-3-Trimethylammonium-Propane (DOTAP):Cholesterol (DOTAP:Chol), which together represented a lipid nanoparticle/DNA complex. The DNA:lipid complex used in this example was produced by mixing, at room temperature, DOTAP:Chol with test DNA (wild-type, M712T, or R266Q pUMVC3-GNE). DOTAP:Chol is a commercially-available lipid particle that is offered by Avanti Polar Lipids, Inc. (Alabaster, Ala.). The DOTAP:Chol was mixed with the pUMVC3-GNE DNA in a manner to achieve the desired total volume, which exhibited a final ratio of 0.5 µg DNA:4 mM DOTAP:Chol, in a final volume of 1 µl.

Intramuscular toxicology. A set of mice (10-12 week old, nominally 20 g BALB/c mice), with each set consisting of 6 female mice and 6 male mice, were provided with either (1) 10 µg (800) of GMP DNA reconstituted in Plasma-Lyte®, (2) 40 µg (80 µl) of GMP DNA reconstituted in Plasma-Lyte®, or (3) 0 µg (80 µl) of GMP DNA (which served as the control and consisted of empty liposomes and Plasma-Lyte®). Another set of mice were not injected at all, and served as an additional control. A single injection was made, the mice were sacrificed at 2 weeks post-injection, and their organs and fluids were harvested. Toxicity was assessed at 24-48 hours, 1 week, and 2 weeks post-injection. Toxicity was assessed based on serum chemistry profiles, CBC analysis, gross toxicity, and immunohistochemistry analysis of muscle tissue.

As shown in FIG. 7, none of the mice provided with the above-described compositions exhibited toxicity at 24 hours, 48 hours, 1 week, or 2 weeks post-injection.

Intravenous toxicology. A set of mice (10-12 week old, nominally 20 g BALB/c mice), with each set consisting of 6 female mice and 6 male mice, were also provided with either (1) 10 µg (200 µl) of GMP DNA reconstituted in Plasma-Lyte®, (2) 40 µg (200 µl) of GMP DNA reconstituted in Plasma-Lyte®, (3) 100 µg (200 µl) of GMP DNA reconstituted in Plasma-Lyte®, or (4) 0 µg (200 µl) of GMP DNA (which served as the control and consisted of empty liposomes and Plasma-Lyte®). An intravenous dose was made, the mice were sacrificed at 2 weeks post-dosage, and their organs and fluids were harvested. Toxicity was assessed at 24-48 hours, 1 week, and 2 weeks post-injection. Toxicity was assessed as described above.

Figure 9:
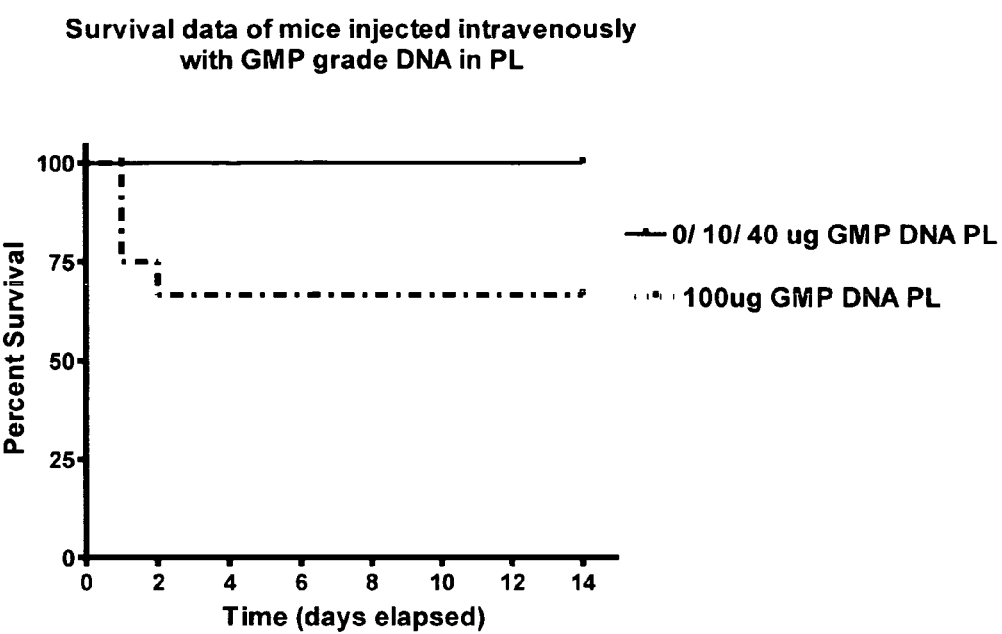
FIG. 9: is a line graph that summarizes the toxicological studies described herein involving intravenous injections of GMP DNA complexes.

As shown in FIG. 8, none of the mice that were provided with 10 μg of GMP DNA exhibited toxicity at 24 hours, 48 hours, 1 week, or 2 weeks post-injection, and only 2 female mice exhibited acute toxicity at 24 hours post-dosage (with all other mice at all other time points not exhibiting any signs of toxicity). Still referring to FIG. 8, three female mice that were provided with 100 μg died at 24 hours post-dosage, and another female mouse died at 48 hours post-dosage. All 6 males exhibited acute toxicity at 24 hours post-dosage. However, these 6 mice all survived, and did not exhibit signs of toxicity at 48 hours, 1 week, or 2 weeks post-dosage. FIG. 9 summarizes the survival data of these mice that were injected intravenously with GMP grade DNA (reconstituted in Plasma-Lyte®).

Comparison of Plasma-Lyte® to Water. In order to identify a preferred carrier in which a GNE-encoding sequence may be disposed, a toxicological comparison was made between Plasma-Lyte® and water. Plasma-Lyte® is a sterile, non-pyrogenic isotonic solution that may be used for intravenous administration. Each 100 mL volume contains 526 mg of Sodium Chloride, USP (NaCl); 502 mg of Sodium Gluconate ($C_6H_{11}NaO_7$); 368 mg of Sodium Acetate Trihydrate, USP ($C_2H_3NaO_2.3H_2O$); 37 mg of Potassium Chloride, USP (KCl); and 30 mg of Magnesium Chloride, USP ($MgCl_2.6H_2O$). It contains no antimicrobial agents. The pH is preferably adjusted with sodium hydroxide to about 7.4 (6.5 to 8.0).

Figure 10:
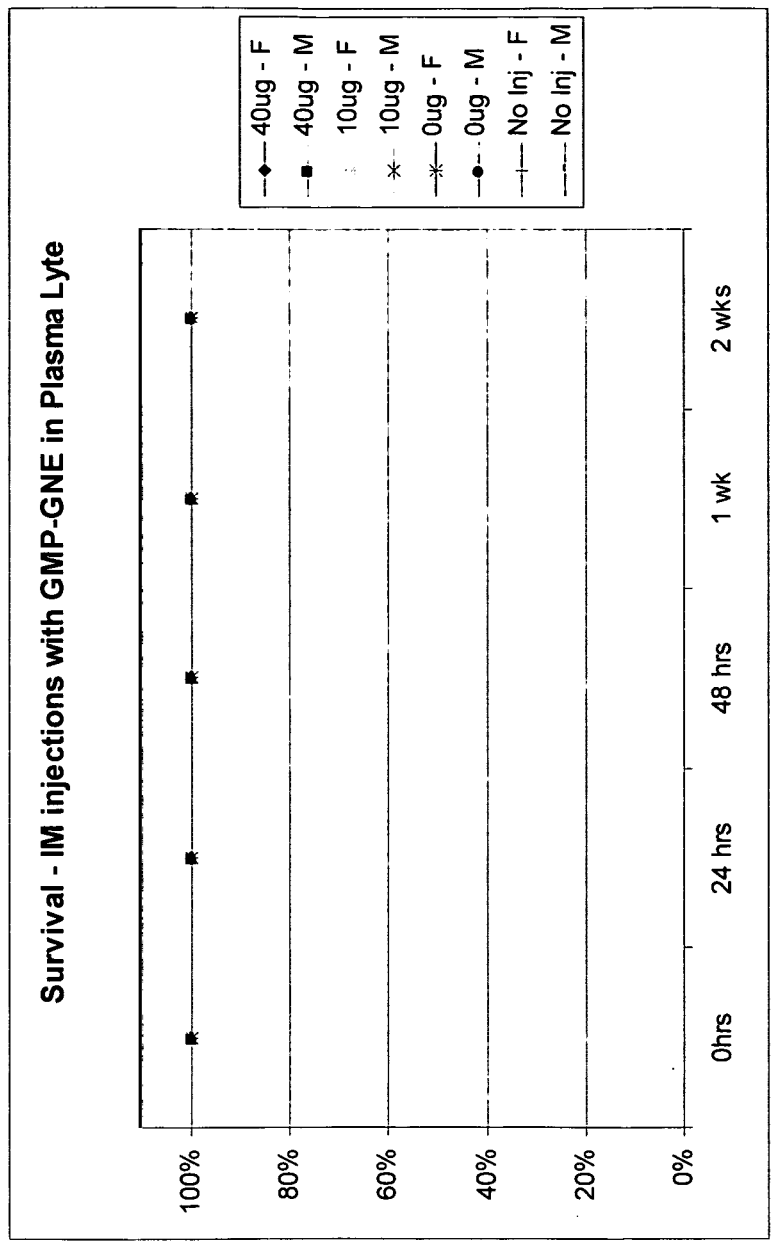
FIG. 10: is a line graph summarizing the survival rate of mice provided with intramuscular injections of GMP-GNE in Plasma-Lyte®.
Figure 11:
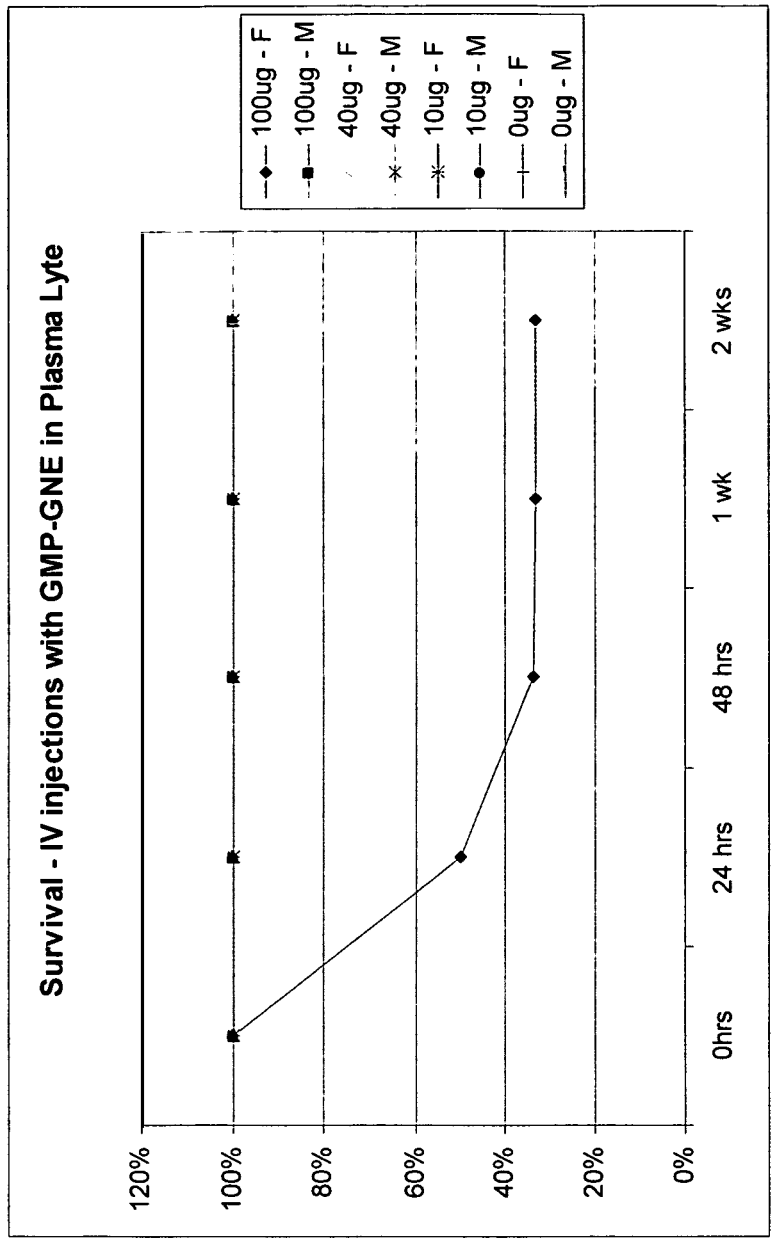
FIG. 11: is a line graph summarizing the survival rate of mice provided with intravenous injections of GMP-GNE in Plasma-Lyte®.
Figure 12:
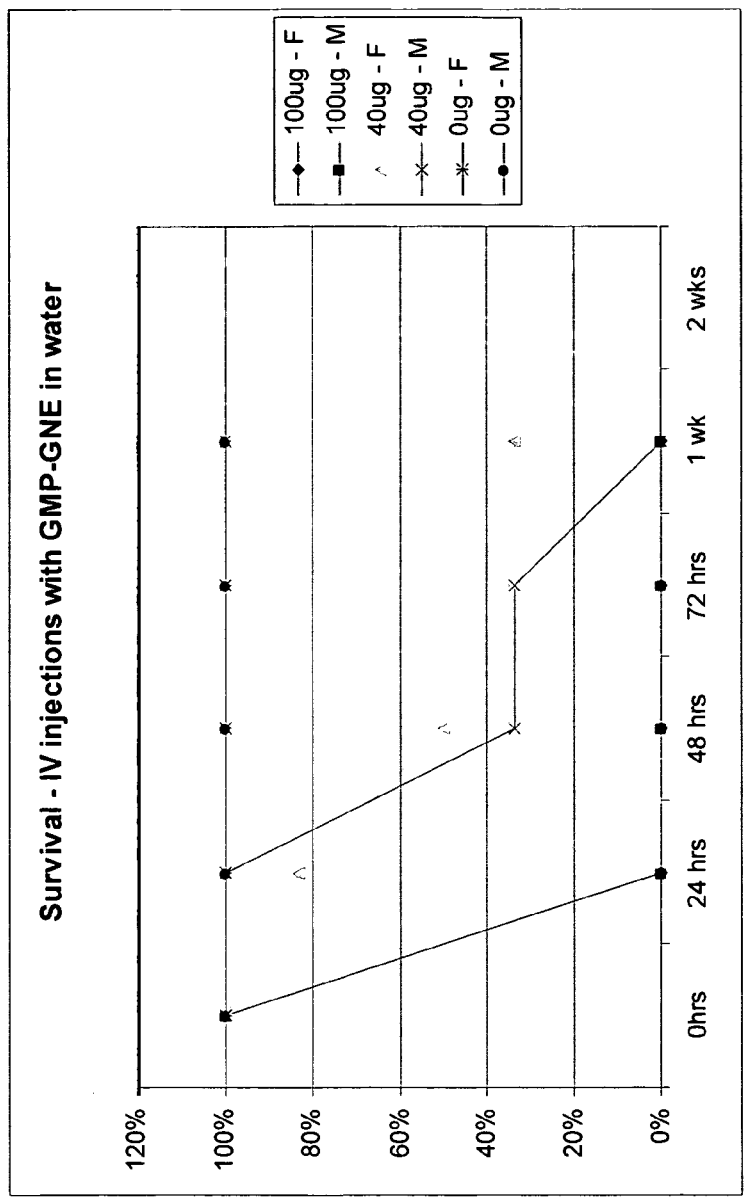
FIG. 12: is a line graph summarizing the survival rate of mice provided with intravenous injections of GMP-GNE in water.

Referring to FIGS. 10-12, a group of four mice were provided with either 40 μg, 10 μg, or 0 μg of GMP-GNE reconstituted in Plasma-Lyte® via intramuscular injections (FIG. 10); 100 μg, 40 μg, 10 μg, or 0 μg GMP-GNE reconstituted in Plasma-Lyte® via intravenous injections (FIG. 11); or 100 μg, 40 μg, or 0 μg GMP-GNE reconstituted in water via intravenous injections (FIG. 12). The GMP-GNE reconstituted in Plasma-Lyte® exhibited significantly improved (lower) toxicological properties (FIGS. 10-11), when compared to the GMP-GNE reconstituted in water (FIG. 12).

GNE Expression in Mice. Three sets of 10-12 week old, nominally 20 g BALB/c mice, with each set including four mice, were provided with intramuscular injections of varying amounts of GNE-encoding compositions, namely, the pUMVC3-wt-DNA construct (FIG. 1), represented by SEQ ID NO: 9, and 1,2-Dioleoyl-3-Trimethylammonium-Propane (DOTAP):Cholesterol—together representing the lipid nanoparticle/GNE-encoding complex described above.

In this example, a first group was injected with 0 μg of GNE-encoding DNA, a second group was injected with 10 μg of GNE-encoding DNA, and a third group was injected with 40 μg of GNE-encoding DNA. At two weeks post-injection, the mice were sacrificed and the injected muscle tissue was harvested.

Next, total RNA was collected from the muscle tissues. The amount of GNE mRNA transcript contained within each sample was next measured via RT-PCR, using GNE-specific primers (and a standard curve was constructed using varying amounts of RNA of known concentration, which was used for extrapolating the quantitative amount of GNE mRNA within each test sample). Table-4 below summarizes the average amount (ng) of GNE mRNA measured by RT-PCR (from two mice within each of the three groups).

TABLE 4

| Dose | Mouse # | ng GNE/mg Muscle | Avg. ng/mg | Std. Dev. | Fold Change |
| --- | --- | --- | --- | --- | --- |
| 0 μg GNE | 32 | 0.00E+00 | 1.36E−09 | 1.92E−09 | 1 |
| | 33 | 2.71E−09 | | | |
| | 34 | | | | |
| | 35 | | | | |
| 10 μg GNE | 8 | | 2.46E−07 | 8.00E−08 | 182 |
| | 9 | | | | |
| | 10 | 3.03E−07 | | | |
| | 11 | 1.90E−07 | | | |
| 40 μg GNE | 20 | | 1.51E−06 | 8.24E−07 | 1115 |
| | 21 | 2.09E−06 | | | |
| | 22 | 9.29E−07 | | | |
| | 23 | | | | |

Figure 13:
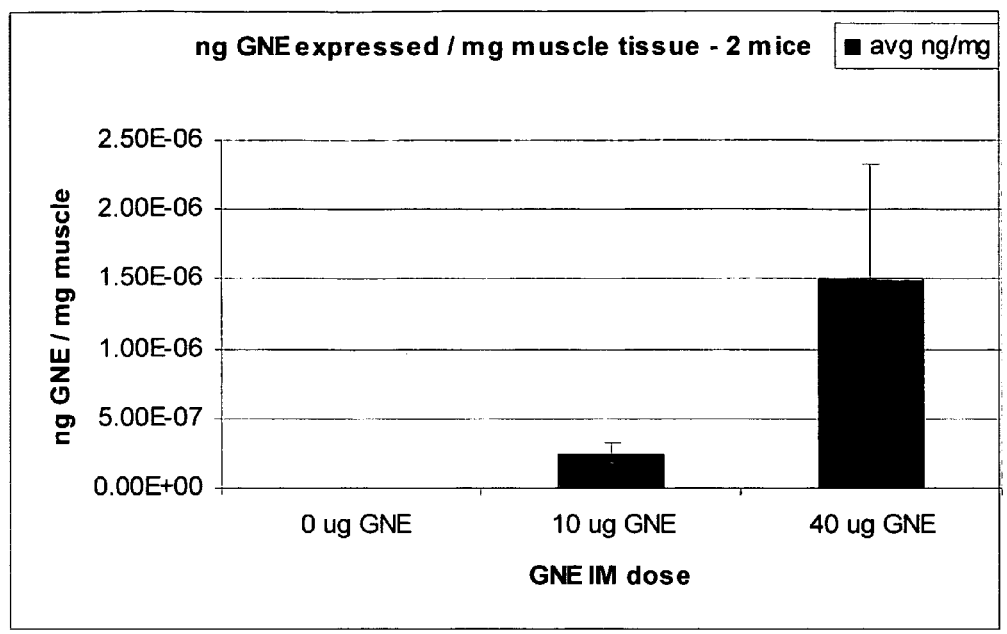
FIG. 13: is a bar graph that summarizes GNE expression in muscle tissue among three different groups of mice provided with varying amounts of GNE-encoding DNA. Each group included two different mice.

These data are further summarized in FIG. 13, which shows the amount of GNE mRNA that was measured for each group (0, 10 and 40 μg of GNE-encoding DNA) normalized against the total amount of muscle tissue from which the RNA was extracted. As shown therein, the 10 μg dose of GNE-encoding DNA resulted in a significant level of GNE expression (a 182-fold increase in GNE expression levels relative to the 0 μg sample), and the 40 μg dose of GNE-encoding DNA resulted in an even greater level of GNE expression (a 1115-fold increase in GNE expression levels relative to the 0 μg sample). These data are consistent with the PCR results shown in the gel of FIG. 14.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for modulating the production of sialic acid in a human, which comprises the steps of:
   providing a human subject in need of treatment of a hereditary inclusion body myopathy;
   providing a vector comprising a liposome or a lipid nanoparticle and a human wild-type GNE-encoding nucleic acid sequence, wherein the wild-type GNE-encoding nucleic acid sequence that comprises SEQ ID NO: 9; and
   providing the vector by intramuscular administration in an amount sufficient to ameliorate the effects of the hereditary inclusion body myopathy local to the site of intramuscular administration in human muscle tissue.

2. The method of claim 1, wherein the wild-type GNE-encoding nucleic acid sequence comprises a promoter operably connected to the wild-type GNE-encoding nucleic acid sequence.

3. The method of claim 2, wherein the promoter is the CMV promoter.

4. The method of claim 2, wherein the wild-type GNE-encoding nucleic acid sequence is disposed within or is connected to a lipid nanoparticle.

5. The method of claim 4, wherein the lipid nanoparticle comprises one or more agents capable of recognizing and binding to a muscle cell or a component thereof.

6. A method for expressing a wild-type GNE in a human with a mutant GNE, wherein the method comprises injecting a the wild-type GNE-encoding sequence within a liposome or lipid nanoparticle that is injected via intramuscular administration at a location in a muscle with hereditary inclusion body myopathy, wherein the wild type GNE-encoding nucleic acid sequence comprises SEQ ID NO: 9.

7. The method of claim 6, wherein the wild-type GNE-encoding nucleic acid sequence comprises a promoter operably connected to the wild-type GNE-encoding nucleic acid sequence.

8. The method of claim 7, wherein the promoter is the CMV promoter.

9. The method of claim 6, wherein the lipid nanoparticle comprises one or more agents capable of recognizing and binding to a muscle cell or a component thereof.

10. A method for ameliorating the effects of Hereditary Inclusion Body Myopathy, which comprises the steps of:
    identifying a human patient with Hereditary Inclusion Body Myopathy; and
    providing a patient with an effective amount of a wild-type GNE-encoding nucleic acid sequence by intramuscular administration at a location with Hereditary Inclusion Body Myopathy, wherein the wild-type GNE-encoding nucleic acid sequence comprises SEQ ID NO: 9 in a liposome or a lipid nanoparticle to ameliorate the effects of the Hereditary Inclusion Body Myopathy in human muscle cells.

11. The method of claim 10, wherein the wild-type GNE-encoding nucleic acid sequence comprises a promoter operably connected to the wild-type GNE-encoding nucleic acid sequence.

12. The method of claim 11, wherein the promoter is the CMV promoter.

13. The method of claim 11, wherein the wild-type GNE-encoding nucleic acid sequence is disposed within or is connected to a lipid nanoparticle.

14. The method of claim 13, wherein the lipid nanoparticle comprises one or more agents capable of recognizing and binding to a muscle cell or a component thereof.

* * * * *